US012630823B2

(12) United States Patent (10) Patent No.: US 12,630,823 B2
Alifragis et al. (45) Date of Patent: \*May 19, 2026

(54) NEURODEGENERATIVE DISORDERS

(71) Applicant: Teesside University, Middlesbrough (GB)

(72) Inventors: Pavlos Alifragis, Egham (GB); Linda Popplewell, Egham (GB); John George Dickson, Egham (GB); Amninder Sangha, Egham (GB)

(73) Assignee: Teesside University, Middlesbrough (GB)

( \* ) Notice: Subject to any disclaimer, the term of this patent is extended or adjusted under 35 U.S.C. 154(b) by 0 days.

This patent is subject to a terminal disclaimer.

(21) Appl. No.: 18/179,325

(22) Filed: Mar. 6, 2023

(65) Prior Publication Data

US 2025/0011772 A1 Jan. 9, 2025

Related U.S. Application Data

(63) Continuation of application No. 16/975,700, filed as application No. PCT/GB2019/050499 on Feb. 25, 2019, now Pat. No. 11,624,066.

(30) Foreign Application Priority Data

Feb. 26, 2018 (GB) .................................... 1803010

(51) Int. Cl.
*C12N 15/113* (2010.01)
*C07K 14/47* (2006.01)

(52) U.S. Cl.
CPC ........ *C12N 15/113* (2013.01); *C07K 14/4711* (2013.01); *C12N 2310/11* (2013.01); *C12N 2310/314* (2013.01); *C12N 2310/315* (2013.01); *C12N 2310/3233* (2013.01); *C12N 2320/33* (2013.01)

(58) Field of Classification Search
CPC .............. C12N 15/113; C12N 2310/11; C12N 2310/315; C12N 2310/3233; C12N 2320/33; C12N 2310/314; C12N 15/111; C07K 14/4711
See application file for complete search history.

(56) References Cited

U.S. PATENT DOCUMENTS

| | | | |
|---|---|---|---|
| 5,187,153 A | 2/1993 | Cordell | |
| 10,655,165 B2 * | 5/2020 | Carlson ................ | C12Q 1/6816 |
| 2003/0023997 A1 | 1/2003 | Peraus | |
| 2012/0122113 A1 | 5/2012 | Prions | |

FOREIGN PATENT DOCUMENTS

| | | |
|---|---|---|
| EP | 1191097 A1 | 3/2002 |
| WO | 2004023973 A3 | 3/2004 |
| WO | 2010120262 A1 | 10/2010 |
| WO | 2012018257 A1 | 2/2012 |
| WO | 2012178122 A3 | 6/2012 |
| WO | 2017064308 A1 | 4/2017 |

OTHER PUBLICATIONS

Siva et al. ("Exon-skipping antisense oligonucleotides to correct missplicing in neurogenetic diseases." Nucleic acid therapeutics 24.1 (2014): 69-86).*
Nguyen, Khue Vu. (β-Amyloid precursor protein (APP) and the human disease AIMS neuroscience 6.4 (2019): 273.).*
Pascal Smith et al., "In vivo regulation of amyloid precursor protein neuronal splicing by microRNAs", J. Neurochemistry, vol. 116, No. 2, Jan. 1, 2011, pp. 240-247, New York, NY.
Eugene V. Makeyev et. al., "The MicoRNA miR-124 promotes neuronal differentiation by triggering brain-specific alternative pre-mRNA splicing", Molecular Cell, vol. 27, No. 3, Aug. 3, 2007, pp. 435-448, Amsterdam, NL.
Xiaomin Yin et al., "Tetrahydroxystilbene glucoside modulates amyloid precursor protein processing via activation of AKT-GSK3β pathway in cells and in APP/PS1 transgenic mice", Biocehm. Biophys. Research Communcations, vol. 495, No. 1, Jan. 1, 2018, pp. 672-678, Amsterdam, NL.
R. Donev et. al., "A role for SC35 and hnRNPA1 in the determination of amyloid precursor protein isoforms", Molecular Psychiatry, vol. 12, No. 7, Mar. 13, 2007, pp. 681-690, GB.
Shafiul Alam et al., "Alternative splicing regulation of APP exon 7 by RBFox proteins", Neurochemistry International, vol. 78, Dec. 1, 2014, pp. 7-17, Amsterdam, NL.
Apostolia Fragkouli et al., "Neuronal ELAVL proteins utilize AUF-1 as a co-partner to induce neuron-specific alternative splicing of APP", Scientific Reports, vol. 7, No. 1, Mar. 14, 2017, Springer Nature.
Todd E. Golde et al., "Expression of β amyloid protein precursor mRNAs: Recognition of a novel alternatively spliced form and quantitation in Alzheimer's disease using PCR" , Neuron, vol. 4, No. 2, Feb. 1, 1990, pp. 253-267, Cell Press, US.
Ling Li et al., "Polymorphic tetranucleotide repeat site within intron 7 of the β-amyloid precursor protein gene and its lack of association with Alzheimer's disease", Hum Genet, vol. 103, 1998, pp. 86-89, Springer-Verlag.
Takeshi Yamada et al., "Neuron-specific splicing of the Alzheimer amyloid precursor protein gene in a mini-gene system", Biochem. Biophys. Res. Comm., vol. 195, No. 1, Aug. 31, 1993, pp. 442-448, Academic Press.
Ioannis Zalachoras et al., "Antisense-mediated RNA targeting: versatile and expedient genetic manipulation in the brain", Frontiers Mol. Neurosci., vol. 4, article 10, Jul. 19, 2011.

(Continued)

*Primary Examiner* — Kimberly Chong
(74) *Attorney, Agent, or Firm* — Ann R. Pokalsky; Wilczynski Brozek Law

(57) ABSTRACT

The invention relates to neurodegenerative disorders, and in particular to novel oligonucleotides for treating such conditions, for example Alzheimer's disease. The invention provides novel antisense oligonucleotides, and compositions comprising such oligos, and therapies and methods for treating neurodegenerative disorders. The invention includes genome editing techniques for achieving similar results as using the novel antisense oligonucleotides.

14 Claims, 9 Drawing Sheets

Specification includes a Sequence Listing.

(56) References Cited

OTHER PUBLICATIONS

Annemieke Aartsma-Rus et al., "Guidelines for antisense oligo-nucleotide design and insight into splice-modulating mechanisms", Mol. Ther., vol. 17, No. 3, Sep. 23, 2008, pp. 548-553, Elsevier.

Annemieke Aartsma-Rus et al., "Antisense-mediated exon skipping: A versatile tool with therapeutic and research applications", RNA, vol. 13, (2007), pp. 1609-1624, Cold Spring Harbor Laboratory Press.

Alvarez-Erviti, et al. Delivery of siRNA to the mouse brain by systemic injection of targeted episomes, Nature Biotechnology 29(4),:341-45, Apr. 2011 (published online Mar. 20, 2011).

Belyaev, et al., The Transcriptionally Active Amyloid Precursor Protein (APP) Intracellular Domain is Preferentially Produced from the 695 Isoform of APP in a β-Secretase-dependent Pathway, The Journal of Biological Chemistry, 285(53): 41443-41545, Dec. 31, 2010.

Bordji, et al., Activation of Extrasynaptic, But Not Synaptic, NMDA Receptors Modifies Amyloid Precursor Protein Expression Pattern and Increases Amyloid-β Production, The Journal of Neuroscience, 30(47):15927-15942, Nov. 24, 2010.

Chiorini, et al., Cloning and Characterization of Adeno-Associated Virus Type 5, Journal of Virology, 73(2):1309-1319, Feb. 1999.

Dayton, et al., The advent of AAV9 expands applications for brain and spinal cord gene delivery, Expert Opin. Biol. Ther., 12(6): 757-766, 2012.

Desmet, et al., Human Splicing Finder: an online bioinformatics tool to predict splicing signals, Nucleic Acids Research. 37(9): 14 pages, doi:10.1093/nar/gkp215, published online Apr. 2009.

Ding, et al., Sfold web server for statistical folding and rational design of nucleic acids, Nucleic Acids Research, 32, Web Server issue: W135-W141, DOI: 10.1093/nar/gkh449, 2004.

Ding, et al., Inhibition of brain tumor growth by intravenous poly (β-L-malic acid) nanobioconjugate with pH dependent drug release, PNAS, 107(42):18143-18148, Oct. 19, 2010.

Egholm et al., PNA hybridizes to complementary oligonucleotides obeying the Watson-Crick hydrogen bonding rules, Nature, 365:566-568, Oct. 7, 1993.

Flammang, et al., Evidence that the Amyloid-β Protein Precursor Intracellular Domain, AICD, Derives from β-Secretase-Generated C-Terminal Fragment, Journal of Alzheimer's Disease, 30:145-153, 2012, DOI10.3233/JAD-2012-112186.

Goldgaber, et al., Characterization and Chromosomal Localization of a cDNA Encoding Brain Amyloid of Alzheimer's Disease, Science, 235:877-880, Feb. 20, 1987, doi10.1242/jcs.048090.

Goodger, et al., Nuclear signaling by the APP intracellular domain occurs predominantly through the amyloidogenic processing pathway, J. Cell Science, 122(20):3703-3714, 2009, doi:10.1242/jcs.048090.

Gorman, et al., Stable alteration of pre-mRNA splicing patterns by modified U7 small nuclear RNAs, Proc. Natl. Acad. Sci., USA, 95:4929-4934, Apr. 1998.

Govindaraju, et al., Backbone-extended pyrrolidine peptide nucleic acids (bepPNA): design, synthesis and DNA/RNA binding studies, The Royal Society of Chemistry, Chem. Comm., 495-497, 2005, published online Dec. 2, 2004, DOI:10.1039/b413542c.

Ho, et al., The Alternatively Spliced Kunitz Protease Inhibitor Domain Alters Amyloid β Protein Precursor Processing and Amyloid β Protein Production in Cultured Cells, J. Biol. Chem., 271(48):30929-30934, 1996.

Huang, et al., Alzheimer Mechanisms and Therapeutic Strategies, Cell, 148: 1204-1222, Mar. 16, 2012.

Hyman, et al., Kunitz Protease Inhibitor-Containing Amyloid β Protein Precursor Immunoreactivity in Alzheimer's Disease, J. Neuropathology and Experimental Neurology, 51(1):76-83, Jan. 1992.

Kang, et al., The precursor of Alzheimer's disease amyloid A4 protein resembles a cell-surface receptor, Nature, 325:733-736, Feb. 19, 1987.

König, et al., Retinoic acid induced differentiated neuroblastoma cells show increased expression of the βA4 amyloid gene of Alzheimer's disease and an altered splicing pattern, FEBS, 29(2):305-310, Sep. 1990.

Matsui, et al., Expression of APP pathway mRNAs and proteins in Alzheimer's Disease, Brain Research 1161:116-123, 2007, doi:10.1016/jbrainres.2007.05.050.

McCarty, et al., Mannitol-facilitated CNS entry of rAAV2 vector signifiantly delayed the neurological disease progression in MPS IIIB mice, Gene Therapy, 16:1340-1352, Jul. 9, 2009.

Moir, et al., Relative Increase in Alzheimer's Disease of Soluble Forms of Cerebral Aβ Amyloid Protein Precursor Containing the Kunitz Protease Inhibitory Domain, J. Biol. Chem., 273(9): 5013-5019, Feb. 27, 1998.

Morita et al., 2'-O,4'-C-Ethylene-bridged nucleic acids (ENA) with nuclease-resistance and high affinity for RNA, Nucleic Acids Research, Supplement No. 1, 241-242, 2001.

Müller, et al., Not just amyloid, physiological functions of the amyloid precursor protein family, Nature Reviews | Neuroscience, doi:10.1038/nm.2017.29, published online Mar. 31, 2017.

Nielsen et al., Sequence-Selective Recognition of DNA by Strand Displacement with a Thymine-Substituted Polyamide, Science 254:1497-1500, Dec. 6, 1991.

Palmert et al., The β-amyloid protein precursor of Alzheimer disease has soluble derivatives found in human brain and cerebro-spinal fluid, Proc. Natl. Acad. Sci., USA, 86:6338-6342, Aug. 1989.

Panegyres et al., The effects of excitotoxicity on the expression of the amyloid precursor protein gene in the brain and its modulation by neuroprotective agents, J. Neural Transm 105:463-478 (1998).

Popplewell, et al., Design of Phosphorodiamidate Morpholino Oligomers (PMOs) for the Induction of Exon Skipping of the Human DMD Gene, Molecular Therapy 17(3):554-561, Mar. 2009.

Rosi et al., Oligonucleotide-Modified Gold Nanoparticles for Intracellular Gene Regulation, Science 312:1027-1029, 2006, DOI:10.1126/science.112559.

Sandbrink et al., APP gene family: unique age-associated changes in splicing of Alzheimer's βA4-amyloid protein precursor, Neurobiology of Disease, 1:13-24, 1994.

Sandbrink, et al., APP Gene Family Alternative Splicing Generates Functionally Related Isoforms, Ann NY Acad Sci 777:281-287, Jan. 17, 1996.

Sandbrink, et al., Expression of the APP Gene Family in Brain Cells, Brain Development and Aging, Gerontology, 43:119-131, 1997.

Schindelin, et al., Fiji: an open-source platform for biological-image analysis, Nature Methods, 9(7):676-682, Jul. 2012, DOI:10.1038/NMETH.2019.

Shariati, et al., Redundancy and divergence in the amyloid precursor protein family, FEBS Letters 587:2036-2045, May 23, 2013.

Smith, et al., In vivo regulation of amyloid precursor protein neuronal splicing by microRNAs, J. Neurochem., 116:240-247, 2011.

Spillantini, et al., Expression and cellular localization of amyloid β-protein precursor transcripts in normal human brain and in Alzheimer's disease, Molecular Brain Research 6:143-150, 1989.

Suter, et al., Double-target antisense U7 snRNAs promote efficint skipping of an aberrant exon in three human β—thalassemic mutations, Human Molecular Genetics, 8(13):2415-2423, 1999.

Tanaka, et al., Three types of amyloid protein precursor mRNA in human brain: their differential expression in Alzheimer's disease, Biochemical and Biophysical Research Communications 157(2):472-479, Dec. 15, 1988.

Tanzi, et al., Amyloid β Protein Gene: cDNA, mRNA Distribution, and Genetic Linkage Near the Alzheimer Locus, Science 235:880-884, 1987.

Thompson, et al., Clustal W: improving the sensitivity of progressive multiple sequence alignment through sequence weighting position-specific gap penalties and weight matrix choice, Nucleic Acids Research, 22(22):4673-4680, 1994.

Thompson, et al., The CLUSTAL_X windows interface: flexible strategies for multple sequence alignment aided by quality analysis tools, Nucleic Acids Research 25(24):4876-4882, 1997.

Vuong, et al., The neurogenetics of alternative splicing, Nature Reviews | Neroscience, 17:265-281, May 2016.

(56)           References Cited

OTHER PUBLICATIONS

Weidemann, et al., Identification, Biogenesis, and Localization of Precursors of Alzheimer's Disease A4 Amyloid Protein, Cell, 57:115-126, Apr. 7, 1989.

Willoughby et al., β-Amyloid Precursor Protein (APP) and APP-RNA Are Rapidly Affected by Glutamate in Cultured Neurons, Journal Molecular Neuroscience, 6:257-276 1995.

Yoshikai, et al., Genomic organization of the human amyloid beta-protein precursor gene, Gene 87:257-263, 1990.

Zhan, et al., APP with Kunitz type protease inhibitor domain (KPI) correlates with neuritic plaque density but not with cortical synaptophysin immunoreactivity in Alzheimer's disease and non-demented aged subjects: a multifactorial analysis, Clin Neuropathol. 14(3):142-149, May-Jun. 1995 (Abstract available only).

Zuker, M., Mfold web server for nucleic acid folding and hybridization prediction, Nucleic Acids Research, 31(13):3406-3415, 2003, DOI:10.1093/nar/gkg595.

Mills et al., Alternative splicing of mRNA in the molecular pathology of neurodegenerative diseases, Neurobiology of Aging 33:1012.e11-1012.e24, 2012, doi:10.1016/j.neurobiolagaing.2011.10.030.

* cited by examiner

Splicing Enhancer Matrices
- SF2/ASF motif
- SRp40 motif
- SC35 motif
- SRp55 motif
ESE-Finder
- ESE- Hexamers  RESCUE-ESE
- PESE - Octamers  Zhang & Chasin Splicing Silencer Matrices
- ESS - motif# 1
- ESS - motif# 2
- ESS - motif# 3
Sironi et al.
- Fas ESS  Wang et al.
- PESS - Octamers  Zhang & Chasin Other
- ESE/ESS octamers relative strength
- Exon

| | exon 7 PMO | exon 8 PMO | exon 7+8 PMO | Control PMO | No PMO |
|---|---|---|---|---|---|
| ▧ NEP | 276.32 | 206.63 | 320.76 | 108.79 | 100 |
| ▧ APP | 214.82 | 245 | 312 | 92 | 100 |

■ NEP  ▨ APP

NEURODEGENERATIVE DISORDERS

CROSS REFERENCE TO RELATED APPLICATIONS

This application is a continuation of U.S. patent application Ser. No. 16/975,700, filed Aug. 25, 2020, now U.S. Pat. No. 11,624,066, which is a 371 application of PCT/GB2019/050499, filed Feb. 25, 2019, the contents of which are incorporated by reference herein as if fully set forth.

REFERENCE TO SEQUENCE LISTING SUBMITTED ELECTRONICALLY

The Sequence Listing associated with this application is filed in electronic format via USPTO Patent Center and is hereby incorporated by reference into the specification in its entirety. The name of the XML file containing the Sequence Listing is: "0268-2001 CON sequenceListing.xml." The date of creation of the Sequence Listing is Mar. 6, 2023, and the size of the file is 38 kb. This sequence listing submitted via Patent Center is part of the specification and is herein incorporated by reference in its entirety.

BACKGROUND OF THE INVENTION

The invention relates to neurodegenerative disorders, and in particular to novel oligonucleotides for treating such conditions, for example Alzheimer's disease. The invention is particularly concerned with novel antisense oligonucleotides, and to compositions comprising such oligos, and to therapies and methods for treating neurodegenerative disorders. The invention extends to the use of genome editing techniques for achieving similar results as using the novel antisense oligonucleotides.

Alternative splicing of mRNAs is a major contributor to the complexity of the brain [1]. Even though the precise function and role of alternatively spliced mRNA transcripts is not fully understood, some of these alternatively spliced mRNAs have been linked to the manifestation and/or progression of neurodegenerative brain disorders [2]. The most common neurodegenerative brain disorder is Alzheimer's disease (AD) and, according to the Alzheimer's society, there are 36 million people with AD worldwide and this figure is expected to double every 20 years. In AD, the functional properties of neurons progressively falter, with significant loss of neuronal projections, connections and ultimately neuronal degeneration. It is believed that a mixture of ageing, genetics and environmental factors contribute to the manifestation and progression of the disease [3].

A characteristic phenotype of AD brains is the presence of extracellular amyloid plaques composed of the deposition of amyloid beta (Aβ) peptides. These peptides are generated as a by-product of the proteolytic processing of the Amyloid Precursor Protein (APP) and are believed to be a significant contributor to the disease [4]. APP in humans is encoded by a single gene of 18 exons [3] that is localized on chromosome 21q21.3 [5, 6] and is expressed in many tissue types [7]. APP belongs to a family of type I single pass transmembrane proteins with a large extracellular domain and a small cytoplasmic tail [8, 9]. Differential splicing of APP mRNA generates several splice variants with the main isoforms producing proteins of 695, 751 and 770 amino acids. The APP695 and APP751 isoforms are produced as a result of splicing out of exons 7 (APP751) or exons 7 and 8 (APP695), respectively, whereas APP770 contains both of these exons [10, 11]. Exon 7 encodes for a Kunitz-type protease inhibitor domain (KPI) and exon 8 encodes for a domain which shares homology with the OX-2 antigen of thymus derived lymphoid cells [10, 11].

Although APP is expressed ubiquitously, the different mRNA variants are expressed at different amounts in different cell types. Non-neuronal cells mostly express APP 751 and 770 [12], whereas APP695 is found in high abundance within neurons [8]. However, in the ageing brain or in the brain of AD patients, as well as in response to NMDA (N-methyl-D-aspartate) receptor stimulation, there is a reduction of APP695 and an increase in the longer isoforms [13-20]. Further support to the hypothesis that a shift in isoform expression is of significance for the progression of AD, comes from a report that shows that the expression of a micro RNA (miR-124) regulating the polypyrimidine tract binding protein PTBP1 (a heterogeneous nuclear ribonucleoprotein responsible for the exclusion of exons 7 and 8 from the mRNA of APP) is reduced in AD patients [21].

Even though the splicing pattern of APP seems to change in AD, the precise function of the three different isoforms is still not clear. Nevertheless, there is evidence linking a shift in the expression levels of the different isoforms in pathological conditions. For instance, prolonged activation of the NMDA glutamate receptors, increases the levels of APP751 but not APP695, increasing also the levels of Aβ [22]. Interestingly, it was further shown that the shift in the expression of APP695 to the APP751 isoform, precedes the increase of Aβ levels suggesting that accumulation of Aβ correlates with an increase of the APP751 isoform [13, 23, 24]. Further to the evidence linking the decrease in the expression of APP695 to the progression of AD, it was also shown that Aβ as well as the APP intracellular domain (AICD), two very important proteolytic products of APP, are preferentially produced from APP695 [25]. This was surprising, since a reduction of APP695 in AD patients would also suggest a decrease in the accumulation of Aβ peptides. A possible explanation of how a reduction in APP695 can contribute to the progression of AD even though the production of Aβ increases, comes from reports showing that the nuclear localisation and subsequent regulation of gene expression from the intracellular AICD fragment is linked to the processing of APP695 by the amyloidogenic pathway [25-28].

Once in the nucleus, AICD displaces histone deacetylases on target genes such as Neprilysin (NEP), a zinc-dependent metalloprotease responsible for the degradation of Aβ [25]. These data suggest that the AICD fragment produced by the proteolytic processing of APP695 regulates the expression of genes that could potentially protect against the toxic effects of Aβ. In this case, increased levels of APP751 in AD patients might trigger the accumulation of Aβ not by inducing the amyloidogenic processing of APP, but rather by disrupting the homeostatic regulation of Aβ levels enhancing its toxicity, through regulation of gene transcription.

In view of the above, there is therefore a need to provide improved therapies for the treatment of neurodegenerative disorders, such as Alzheimer's disease.

BRIEF SUMMARY OF THE INVENTION

As described in the Examples, the inventors have investigated how complementary, modified antisense oligonucleotides (AONs) can target the processing of APP mRNA to promote the exclusion of exons 7 and 8 via exon skipping. They designed phosphorodiamidate morpholino oligomers (PMOs) complementary to various sites within exons 7 and 8, and also around the splice junctions of exons 7 and 8, and tested them in the human neuroblastoma cell line SH-SY5Y to identify the best candidate sequences. Remarkably, the results showed complete skipping of both exons 7 and 8 at the mRNA levels after 48 hours, and a substantial increase of the shorter isoform, APP695, at the protein level after 72 hours. These results show the feasibility of using antisense oligonucleotides to alter the processing of APP mRNA, providing an alternative therapeutic approach to AD.

Thus, in a first aspect of the invention, there is provided an antisense oligonucleotide (AON) capable of reducing or preventing exon 7 and/or exon 8 inclusion into an amyloid precursor protein (APP) mRNA produced by splicing from an APP transcript.

Advantageously, and preferably, the Examples describe how the AON according to the first aspect can be used to promote exon skipping to increase the expression of the APP695 mRNA isoform, and reduce the amount of the APP751 and APP770 isoforms. The primary goal was to design AONs that target two alternatively spliced exons of APP, i.e. exons 7 and 8. The inventors designed five AONs targeting exon 7, and four AONs targeting exon 8. Two of the most potent PMOs were selected, one for each exon (PMO 7.2 and PMO 8.2), and the inventors showed that it is surprisingly possible to achieve 100% skipping of the targeted exons at relatively low AON concentrations.

Moreover, the inventors also showed that the abundancy of APP695 that was observed at the mRNA level was also apparent at the protein level when the AONs were used in combination. The data clearly demonstrate that restoration of APP695 levels in vitro using AONs is feasible, and so one can be optimistic of the implementation of the strategies described herein as a therapeutic approach to neurodegenerative disorders, such as Alzheimer's Disease.

In a second aspect, there is provided an antisense oligonucleotide (AON) according to the first aspect, for use in therapy or diagnosis.

In a third aspect, there is provided an antisense oligonucleotide (AON) according to the first aspect, for use in treating, preventing or ameliorating a neurodegenerative disorder.

In a fourth aspect, there is provided a method of treating, ameliorating or preventing a neurodegenerative disorder in a subject, the method comprising, administering to a subject in need of such treatment, a therapeutically effective amount of an antisense oligonucleotide (AON) according to the first aspect.

Preferably, the neurodegenerative disorder is Alzheimer's disease.

DETAILED DESCRIPTION OF THE INVENTION

As described herein, the inventors have developed an effective strategy which modifies the ratio of APP splice variants rather than reducing the amount of expression overall. As such, the strategy is based on allowing the expression of APP, and increasing the relative concentration of the APP695 isoform (which lacks exons 7 and 8), while simultaneously decreasing the amount of the APP751 isoform (which lacks exon 7 but includes exon 8) and APP770 isoform (which includes both exon 7 and 8), by skipping exons 7 and/or 8 in any APP pre-mRNA isoform that is known to exist. A strategy that is used to alter gene expression and the production of a specific protein is the use of modified antisense oligonucleotides (AONs) according to the invention, that bind to a target region, preferably in standard Watson-Crick fashion, to interfere with RNA transcription, pre-mRNA splicing or mRNA translation. AONs that cause the skip of exons that harbor pathologic mutations are currently being trialed to treat Duchenne Muscular Dystrophy (DMD). A pre-requisite for this approach is that the exons flanking the exon(s) to be skipped are in frame. In other words, joining of flanking exons should not interrupt the reading frame of the full length protein, to avoid incorporation of downstream codons coding for different amino acids than the wild-type protein, or even stop codons.

Preferably, in one embodiment, the antisense oligonucleotide (AON) of the invention is capable of reducing or preventing exon 7 inclusion into an amyloid precursor protein (APP) mRNA produced by splicing from an APP transcript. Preferably, therefore, the AON is used for exon 7 skipping for treating, ameliorating or preventing the neurodegenerative disorder. The nucleotide sequence of one embodiment of exon 7 of the human amyloid precursor protein (APP) gene (RefSeq: NM_000484.3) is 168 nucleotides in length, and is provided herein as SEQ ID No: 1, as follows:

```
                                      [SEQ ID No: 1]
AGGTGTGCTCTGAACAAGCCGAGACGGGGCCGTGCCGAGCAATGATCTC

CCGCTGGTACTTTGATGTGACTGAAGGGAAGTGTGCCCCATTCTTTTAC

GGCGGATGTGGCGGCAACCGGAACAACTTTGACACAGAAGAGTACTGCA

TGGCCGTGTGTGGCAGCGCCA
```

The peptide sequence encoded by one embodiment of exon 7 of the APP protein is 57 amino acids in length, and is provided herein as SEQ ID No: 2, as follows:

```
                                      [SEQ ID No: 2]
EVCSEQAETGPCRAMISRWYFDVTEGKCAPFFYGGCGGNRNNFDTEEYC

MAVCGSAM
```

Preferably, in another embodiment, the antisense oligonucleotide (AON) is capable of reducing or preventing exon 8 inclusion into an amyloid precursor protein (APP) mRNA produced by splicing from an APP transcript. Preferably, therefore, the AON is used for exon 8 skipping for treating, ameliorating or preventing the neurodegenerative disorder. The nucleotide sequence of one embodiment of exon 8 of the human APP gene is 57 nucleotides in length, and is provided herein as SEQ ID No: 3, as follows:

```
                                      [SEQ ID No: 3]
TGTCCCAAAGTTTACTCAAGACTACCCAGGAACCTCTTGCCCGAGATCC

TGTTAAAC
```

The peptide sequence encoded by one embodiment of exon 8 of the APP protein is 20 amino acids in length, and is provided herein as SEQ ID No: 4, as follows:

```
                                      [SEQ ID No: 4]
          MSQSLLKTTQEPLARDPVKL
```

The inventors of the present invention sought to exploit the potential of exon skipping AONs as an elegant strategy to address neurodegenerative disorders, such as Alzheimer's disease. The approach exploits skipping exon 7 and/or 8 of APP (numbered according to the canonical nomenclature of APP). In a most preferred embodiment, at least two AONs are used, a first AON which reduces or prevents exon 7 inclusion into an APP mRNA produced by splicing from an APP transcript, and a second AON which reduces or prevents exon 8 inclusion into an APP mRNA. In this scenario, a protein made by skipping exon 7 and 8 preferably comprises the following features:

1) exon 6 is joined with exon 9, maintaining the reading frame and resulting in a protein with 695 amino acids, which is named "APP695" herein;

2) the Kunitz-type protease inhibitor domain (KPI), which is within exon 7, is removed; and/or 3) a domain sharing homology with the OX-2 antigen of thymus-derived lymphoid cells, which is within exon 8, is removed.

The process harnessed herein is known to occur in nature in an overwhelming number of genes, under the influence of factors associated with the differentiation state of a cell, age, nutritional state and other chemical or biological factors. Pre-mRNA splicing can also be manipulated at will, for example by modulating splice site selection by the endogenous splicing machinery. Splice site selection can, for example, be modulated using AONs that interfere with binding of components of the splicing machinery to a splice site, a so-called branch point, a polypyrimidine tract, and/or regions affecting splice site selection. Such regions are known as splicing enhancers and splicing silencers, which may be located either in exons or introns. Hence, there are intronic and exonic splice site enhancers (ISEs and ESEs) and intronic or exonic splice site silencers (ISSs and ESSs). It is also possible to modulate splicing in a (semi)-quantitative fashion.

The inventors have tested a number of AONs binding to target regions located inside exons 7 and 8, as well as to sequences bridging intron 6-7 and exon 7, sequences bridging exon 7 and intron 7-8, sequences bridging intron 7-8 and exon 8, and sequences bridging exon 8 and intron 8-9. It should be appreciated that the introns are named according to the exons that they separate, i.e. intron 6-7 is the intron between exon 6 and exon 7, intron 7-8 is the intron between exon 7 and exon 8, and intron 8-9 is the intron between exon 8 and exon 9.

Preferably, therefore, the AON of the first aspect is capable of binding to and/or is complementary to a target region within:

(i) the 3' part of intron 6-7 and/or the 5' part of exon 7 of the APP gene;

(ii) exon 7 of the APP gene;

(iii) the 3' part of exon 7 and/or the 5' part of intron 7-8 of the APP gene;

(iv) the 3' part of intron 7-8 and/or the 5' part of exon 8 of the APP gene;

(v) exon 8 of the APP gene; and/or (vi) the 3' part of exon 8 and/or the 5' part of intron 8-9 of the APP gene.

In one preferred embodiment, the AON has at most 4 or fewer mismatches with its complementary target region, preferably 3 or fewer, more preferably 2 or fewer, even more preferably 1 or no mismatches.

In a further preferred embodiment, the AON is complementary to at least 8 nucleotides in the target region, preferably from 8 to 50 nucleotides, more preferably from 12 to 50 nucleotides, in the target region.

In one embodiment, the AON has a length of from 18 to 42 nucleotides, preferably from 22 to 42, more preferably from 27 to 39 nucleotides in length.

In an embodiment in which the antisense oligonucleotide (AON) is capable of reducing or preventing exon 7 inclusion into an APP mRNA produced by splicing from an APP transcript (i.e. results in exon 7 skipping), the target region for the AON is between 150 nucleotides upstream of the intron 6/exon 7 junction (−150) and 150 nucleotides downstream of the exon 7/intron 7 junction (+150). The nucleotide sequence of one embodiment of the target region for the AON is provided herein as SEQ ID No: 27, as follows (in which the bases in capital letters denote exon 7, and the lowercase bases denote the introns either side):

[SEQ ID No: 27]
taaattcctcagtaaatgtttggtagatgctgcctaataaaccagtcca ggttgccactgggaggattaaaagaagtaaacgtgtatacatgaacaga gagacagtgccttttcatgctaaatgtggttccccacatctcctctgat tagAGGTGTGCTCTGAACAAGCCGAGACGGGGCCGTGCCGAGCAATGAT

CTCCCGCTGGTACTTTGATGTGACTGAAGGGAAGTGTGCCCCATTCTTT

TACGGCGGATGTGGCGGCAACCGGAACAACTTTGACACAGAAGAGTACT

GCATGGCCGTGTGTGGCAGCGCCAgtaagtggacccttcttcgagcctg gccacctttcgtctctctcgccactgactctgcttttgtaacagattg attttcctggttcttgggaatgggcctgttgctaccactaaccacattt ctgtccacttctctaattgctcagagt Hence, preferably the nucleotide sequence of the target region for the AON substantially comprises SEQ ID No: 27, or a fragment or variant thereof.

In a preferred embodiment, the AON target region spans 15 nucleotides upstream and 150 nucleotides downstream of exon 7 of the human APP gene (−15 to +50), and is represented as SEQ ID NO: 5 (as represented in FIG. 2).

In one embodiment, the nucleotide sequence of the AON (called "PMO 7.1") is 30 nucleotides in length, and is provided herein as SEQ ID No: 6, as follows:

[SEQ ID No: 6]
ACGGCCCCGTCTCGGCTTGTTCAGAGCACA

In one embodiment, the nucleotide sequence of the AON (called "PMO 7.2") is 30 nucleotides in length, and is provided herein as SEQ ID No: 7, as follows:

[SEQ ID No: 7]
CACACTTCCCTTCAGTCACATCAAAGTACC

In one embodiment, the nucleotide sequence of the AON (called "PMO 7.3") is 30 nucleotides in length, and is provided herein as SEQ ID No: 8, as follows:

[SEQ ID No: 8]
TTGTTCCGGTTGCCGCCACATCCGCCGTAA

In one embodiment, the nucleotide sequence of the AON (called "PMO 7.4") is 30 nucleotides in length, and is provided herein as SEQ ID No: 9, as follows:

[SEQ ID No: 9]
ACGGCCATGCAGTACTCTTCTGTGTCAAAG

In one embodiment, the nucleotide sequence of the AON (called "PMO 7.5") is 30 nucleotides in length, and is provided herein as SEQ ID No: 10, as follows (in which the bases in capital letters denote exon 7 targeting bases, and the lowercase bases denote intron targeting bases):

[SEQ ID No: 10]
caggctcgaagaagggtccacttacTGGCG

Thus, in a particularly preferred embodiment, the AON is complementary to a target region within, or adjacent to, exon 7, and comprises a nucleotide sequence selected from the group consisting of SEQ ID NO: 6, 7, 8, 9 and 10. In a most preferred embodiment, the AON comprises a nucleotide sequence selected from SEQ ID NO: 6, 7, 8 and 9. The most effective AON for conferring exon 7 skipping was PMO 7.2, and so SEQ ID No: 7 is the most preferred.

Hence, in yet another aspect of the present invention, there is provided an AON capable of reducing or preventing exon 7 inclusion into an APP mRNA produced by splicing from an APP transcript, wherein the AON is capable of binding to and/or is complementary to a target region within SEQ ID NO: 5, optionally wherein the AON comprises a nucleotide sequence selected from SEQ ID NO: 6, 7, 8, 9 or 10.

In another preferred aspect, the AON according to the present invention comprises a nucleotide sequence that is complementary to at least 8 nucleotides within the sequence of SEQ ID NO: 5, and wherein the oligonucleotide comprises the sequence of SEQ ID NO: 6, 7, 8, 9 or 10.

In an embodiment in which the antisense oligonucleotide (AON) is capable of reducing or preventing exon 8 inclusion into an APP mRNA produced by splicing from an APP transcript (i.e. results in exon 8 skipping), the target region for the AON is between 150 nucleotides upstream of the intron 7/exon 8 junction (−150) and 150 nucleotides downstream of the exon 8/intron 8 junction (+150). The nucleotide sequence of one embodiment of the target region for the AON is provided herein as SEQ ID NO: 28, as follows (in which the bases in capital letters denote exon 8, and the lowercase bases denote the introns either side):

[SEQ ID No: 28]
atgttcattttggttttgttggagggaccaaacctaagtgagtgattt gtttgttaggttgttttttttgtcagtggactcgtgcatttcagccatca ttcccatgtttctctttttgtttttagttatgttctcttattttttcca tagTGTCCCAAAGTTTACTCAAGACTACCCAGGAACCTCTTGCCCGAGA TCCTGTTAAACgtacgttgtcattcacctgagggaagggaagaggggag gaggatgctgcttggttcacataactccagcatcatcaccttctttgca tggttttgtgtttcttgaacacctgtcttagtaaaatgtttcttcccat taccttgcttgtaa Hence, preferably the nucleotide sequence of the target region for the AON substantially comprises SEQ ID No: 28, or a fragment or variant thereof.

In a preferred embodiment, the AON target region spans nucleotides 50 nucleotides upstream and 50 nucleotides downstream of exon 8 of the human APP gene (−50 to +50), and is represented as SEQ ID NO: 11 (as represented in FIG. 2).

In one embodiment, the nucleotide sequence of the AON (called "PMO 8.1") is 25 nucleotides in length, and is provided herein as SEQ ID No: 12, as follows (in which the bases in capital letters denote exon 8 targeting bases, and the lowercase bases denote intron targeting bases):

[SEQ ID No: 12]
AAACTTTGGGACActatggaaaaaa

In one embodiment, the nucleotide sequence of the AON (called "PMO 8.2") is 25 nucleotides in length, and is provided herein as SEQ ID No: 13, as follows:

[SEQ ID No: 13]
AAGAGGTTCCTGGGTAGTCTTGAGT

In one embodiment, the nucleotide sequence of the AON (called "PMO 8.3") is 25 nucleotides in length, and is provided herein as SEQ ID No: 14, as follows (in which the bases in capital letters denote exon 8 targeting bases, and the lowercase bases denote intron targeting bases):

[SEQ ID No: 14]
acgtacGTTTAACAGGATCTCGGGC

In one embodiment, the nucleotide sequence of the AON (called "PMO 8.4") is 25 nucleotides in length, and is provided herein as SEQ ID No: 15, as follows:

[SEQ ID No: 15]
cttcccttccctcaggtgaatgaca

Thus, in a particularly preferred embodiment, the AON is complementary to a target region within, or adjacent to, exon 8, and comprises a nucleotide sequence selected from the group consisting of SEQ ID NO: 12, 13, 14 and 15. In a most preferred embodiment, the AON comprises a nucleotide sequence selected from SEQ ID NO: 12 and 13. The most effective AON for conferring exon 8 skipping was PMO 8.2, and so SEQ ID No: 13 is the most preferred.

Hence, in yet another aspect of the present invention, there is provided an AON capable of reducing or preventing exon 8 inclusion into an APP mRNA produced by splicing from an APP transcript, wherein the AON is capable of binding to and/or is complementary to a target region within SEQ ID NO: 11, optionally wherein the AON comprises a nucleotide sequence selected from SEQ ID NO: 12, 13, 14 or 15.

In another preferred aspect, the AON according to the present invention comprises a nucleotide sequence that is complementary to at least 8 nucleotides within the sequence of SEQ ID NO: 11, and wherein the oligonucleotide comprises the sequence of SEQ ID NO: 12, 13, 14 or 15.

In a fifth aspect, there is provided an antisense oligonucleotide (AON) comprising a nucleotide sequence selected from the group consisting of: SEQ ID NO: 6, 7, 8, 9, 10, 12, 13, 14 and 15.

When used in therapy to treat the neurodegenerative disorder, it is preferred that one or more AON for causing exon 7 skipping is used in combination with one or more AON for causing exon 8 skipping. For example, preferably any one of the AON comprising a nucleotide sequence selected from the group consisting of SEQ ID NO: 6, 7, 8, 9 and 10, which have been shown to cause exon 7 skipping, may be used in combination with any one of the AON comprising a nucleotide sequence selected from the group consisting of SEQ ID NO: 12, 13, 14 or 15, which have been shown to cause exon 8 skipping. The most preferred exon 7 skipping AON is SEQ ID No: 7, and the most preferred exon 8 skipping AON is SEQ ID No: 13, and so these are most preferably used in combination with each other.

In a sixth aspect, the invention also provides a method for preventing or reducing exon 7 and/or exon 8 inclusion into a human APP mRNA, when said mRNA is produced by splicing from an RNA transcript, the method comprising contacting one or more AON according to the invention with a cell, a tissue, in vitro or ex vivo, or a living human subject comprising such a cell, under conditions conducive to uptake of the one or more AON by such cell, and allowing splicing to take place.

In a seventh aspect, the invention also relates to a method for making an internally truncated human APP protein lacking the region encoded by exon 7 and/or exon 8 in a human APP gene, the method comprising contacting one or more AON according to the invention with a cell that expresses the human APP gene, under conditions conducive to uptake of the one or more AON, allowing the APP gene to be expressed, whereby the APP pre-mRNA is spliced by the splicing machinery of the cell, thereby producing mRNAs, wherein exon 7 and/or exon 8 is not included, and allowing said mRNA to be translated into the internally truncated protein.

In a preferred embodiment, the method of the seventh aspect is carried out in a subject's brain.

In a preferred embodiment, the internally truncated human APP protein is human APP695.

The invention allows designing an oligonucleotide with acceptable RNA binding kinetics and/or thermodynamic properties. The RNA binding kinetics and/or thermodynamic properties are at least in part determined by the melting temperature of an oligonucleotide (Tm; calculated with the oligonucleotide properties calculator (www.unc.edu/~cail/biotool/oligo/index.html) for single stranded RNA using the basic Tm and the nearest neighbor models), and/or the free energy of the AON-target exon complex (using RNA structure version 4.5). If a Tm is too high, the oligonucleotide is expected to be less specific. An acceptable Tm and free energy depend on the sequence of the oligonucleotide, the chemistry of the backbone (phosphodiester, phosphorothioate, phosphoramidate, peptide-nucleic acid, etc.), the nature of the sugar moiety (ribose, deoxyribose, substituted ribose, intra-molecular bridge) and chemical modification of the nucleobase. Therefore, the range of Tm can vary widely.

Preferably, the AON causes an exon skipping rate of at least 50%, 60%, 70% or 80%. More preferably, the AON causes an exon skipping rate of at least 90%, 95%, 97%, 98%, 99% or 100%.

The exon skipping percentage or efficiency may be calculated by determining the concentration of all bands amplified, divided by the concentration of the shortened (exon 7 and/or exon 8-free) band amplified, after a given number of PCR cycles, times 100%, for any given primer set, provided the number of cycles is such that the amplification is still in the exponential phase. Quantification can be performed using the Agilent 2100 Bioanalyzer in combination with DNA1000 kit, though the skilled person would appreciate other standard methods which could be used.

Preferably, an AON according to the invention, which comprises a sequence that is complementary to a nucleotide target region as shown in SEQ ID NO: 5 (exon 7) or 11 (exon 8) is such that the complementary part is at least about 80%, more preferably at least about 90%, still more preferably at least about 95%, even more preferably at least about 98%, and most preferably about 100% complementary to the target sequence. It is thus not absolutely required that all the bases in the region of complementarity are capable of pairing with bases in the opposing strand. For instance, when designing the oligonucleotide, one may want to incorporate a residue that does not base pair with the base on the complementary strand. Mismatches may, to some extent, be allowed, if under the circumstances in the cell, the stretch of nucleotides is sufficiently capable of hybridizing to the complementary part. In this context, "sufficiently" can mean that the AONs according to the invention are capable of inducing exon skipping of exon 7 and/or exon 8.

Skipping the targeted exon may conveniently be assessed by PCR/Bioanalyzer, optionally ddPCR. The complementary regions are preferably designed such that, when combined, they are specific for the exon in the pre-mRNA. Such specificity may be created with various lengths of complementary regions as this depends on the actual sequences in other (pre-mRNA molecules in the system. The risk that the oligonucleotide also will be able to hybridize to one or more other pre-mRNA molecules decreases with increasing size of the oligonucleotide, while the length should not be too long to create problems with manufacturability, purification and/or analytics.

It is clear that oligonucleotides comprising mismatches in the region of complementarity but that retain the capacity to hybridize and/or bind to the targeted region(s) in the pre-mRNA, can be used in the present invention. However, preferably at least the complementary parts do not comprise such mismatches as these typically have a higher efficiency and a higher specificity, than oligonucleotides having such mismatches in one or more complementary regions. It is thought, that higher hybridization strengths, (i.e. increasing number of interactions with the opposing strand) are favorable in increasing the efficiency of the process of interfering with the splicing machinery of the system. Preferably, the complementarity is from 90% to 100%. In general, this allows for 1 or 2 mismatches in an oligonucleotide of 20 nucleotides, and 5 or fewer in an AON of 50 nucleotides.

An AON according to the invention may be longer than the complementary region on the target, having non-base pairing ends or 'overhanging' ends. It is preferred that such 'overhang', which may be on the 5' site or the 3' site or both, should be kept to a minimum, as non-complementary bases at the ends of the AON may reduce the specificity of binding and/or the strength of binding of the AON to the target.

Preferably, the length of the complementary part of the oligonucleotide is the same as the length of the oligonucleotide, meaning there are no 5' or 3' ends of the oligo that do not form a base pair with the target NA. Thus, a preferred length for an oligonucleotide of the invention is 50 nucleotides or less, e.g. 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47 or 48 nucleotides. Particularly good results have been obtained with AONs having a length of 20 to 35 nucleotides, more in particular having a length of 25 or 30 nucleotides. An exon skipping AON according to the invention may contain one or more DNA nucleotides (consequently a RNA "u" residue will be a "t" residue as DNA counterpart), but ideally does not consist solely of DNA nucleotides (due to poor or absent effects). RNA oligonucleotides (including modified RNA) are preferred for exon skipping purposes.

Total knock down of APP RNA has never been tested in humans and may be associated with severe adverse effects. Therefore, exon skipping AONs that do not cause significant, let alone total, APP RNA knock down, are strongly preferred according to the invention. siRNAs aimed at destruction, so-called 'gapmers' invoking RNase H mediated break-down, or any other AONs causing total knockdown of APP are not preferred, according to the invention.

It is preferred that an exon skipping AON of the invention comprises one or more nucleotides that is/are modified to increase nuclease resistance, and/or to increase the affinity of the AON for the target sequence. Therefore, in a preferred embodiment, the AON sequence comprises at least one nucleotide analogue or equivalent, wherein a nucleotide analogue or equivalent is defined as a residue having a modified base, and/or a modified backbone, and/or a non-natural internucleoside linkage, or a combination of these modifications.

Preferred AONs are oligoribonucleotides, and ideally these have internucleosidic linkages which are chemically modified (preferably with phosphorothioate-linkages).

Modification of the ribose sugar is also useful, e.g. with a 2'-O-alkyl modification (ideally 2'-O-methyl).

In a preferred embodiment, the nucleotide analogue or equivalent comprises a modified backbone. Examples of such backbones are provided by morpholino backbones, carbamate backbones, siloxane backbones, sulfide, sulfoxide and sulfone backbones, formacetyl and thioformacetyl backbones, methyleneformacetyl backbones, riboacetyl backbones, alkene containing backbones, sulfamate, sulfonate and sulfonamide backbones, methyleneimino and methylenehydrazino backbones, and amide backbones. Phosphorodiamidate morpholino oligomers are modified backbone oligonucleotides that have previously been investigated as antisense agents. Tricyclo DNA and peptide conjugated backbones are also envisaged.

Morpholino oligonucleotides have an uncharged backbone in which the deoxyribose sugar of DNA is replaced by a six membered ring and the phosphodiester linkage is replaced by a phosphorodiamidate linkage. Morpholino oligonucleotides are resistant to enzymatic degradation and appear to function as antisense agents by arresting translation or interfering with pre-mRNA splicing rather than by activating RNase H. Morpholino oligonucleotides have been successfully delivered to tissue culture cells by methods that physically disrupt the cell membrane, and one study comparing several of these methods found that scrape loading was the most efficient method of delivery. However, because the morpholino backbone is uncharged, cationic lipids are not effective mediators of morpholino oligonucleotide uptake in cells. According to one embodiment of the invention the linkage between the residues in a backbone do not include a phosphorus atom, such as a linkage that is formed by short chain alkyl or cycloalkyl internucleoside linkages, mixed heteroatom and alkyl or cycloalkyl internucleoside linkages, or one or more short chain heteroatomic or heterocyclic internucleoside linkages. In accordance with this embodiment, a preferred nucleotide analogue or equivalent comprises a Peptide Nucleic Acid (PNA), having a modified polyamide backbone [29]. PNA-based molecules are true mimics of DNA molecules in terms of base-pair recognition. The backbone of the PNA is composed of N-(2-aminoethyl)-glycine units linked by peptide bonds, wherein the nucleobases are linked to the backbone by methylene carbonyl bonds. An alternative backbone comprises a one-carbon extended pyrrolidine PNA monomer [30]. Since the backbone of a PNA molecule contains no charged phosphate groups, PNA-NA hybrids are usually more stable than RNA-RNA or RNA-DNA hybrids, respectively [31].

According to another embodiment of the invention, the backbone comprises a morpholino nucleotide analog or equivalent, in which the ribose or deoxyribose sugar is replaced by a 6-membered morpholino ring. A most preferred nucleotide analog or equivalent comprises a phosphorodiamidate morpholino oligomer (PMO), in which the ribose or deoxyribose sugar is replaced by a 6-membered morpholino ring, and the anionic phosphodiester linkage between adjacent morpholino rings is replaced by a non-ionic phosphorodiamidate linkage.

In yet a further embodiment, a nucleotide analogue or equivalent of the invention comprises a substitution of one of the non-bridging oxygens in the phosphodiester linkage. This modification slightly destabilizes base-pairing but adds significant resistance to nuclease degradation. A preferred nucleotide analogue or equivalent comprises phosphorothioate, chiral phosphorothioate, phosphorodithioate, phosphotriester, aminoalkylphosphotriester, H-phosphonate, methyl and other alkyl phosphonate including 3'-alkylene phosphonate, 5'-alkylene phosphonate and chiral phosphonate, phosphinate, phosphoramidate including 3'-amino phosphoramidate and aminoalkylphosphoramidate, thiono-phosphoramidate, thionoalkylphosphonate, thionoalkylphosphotriester, selenophosphate or boranophosphate.

A further preferred nucleotide analogue or equivalent of the invention comprises one or more sugar moieties that are mono- or di-substituted at the 2', 3' and/or 5' position such as a —OH; —F; substituted or unsubstituted, linear or branched lower (C1-C10) alkyl, alkenyl, alkynyl, alkanyl, allyl, or aralkyl, that may be interrupted by one or more heteroatoms; O-, S-, or N-alkyl; O-, S-, or N-alkenyl; O-, S- or N-alkynyl; O-, S-, or N-allyl; O-alkyl-O-alkyl, -methoxy, -aminopropoxy; methoxyethoxy; -dimethylaminooxy-ethoxy; and -dimethylaminoethoxyethoxy. The sugar moiety can be a furanose or derivative thereof, or a deoxyfuranose or derivative thereof, preferably ribose or derivative thereof, or deoxyribose or derivative thereof. A preferred derivatized sugar moiety comprises a Locked Nucleic Acid (LNA), in which the 2'-carbon atom is linked to the 3' or 4' carbon atom of the sugar ring thereby forming a bicyclic sugar moiety. A preferred LNA comprises 2'-O, 4'-C-ethylene-bridged nucleic acid [32]. These substitutions render the nucleotide analogue or equivalent RNase H and nuclease resistant and increase the affinity for the target RNA.

It is understood by a skilled person that it is not necessary for all internucleosidic linkages in an AON to be modified. For example, some internucleosidic linkages may be unmodified, whereas other internucleosidic linkages are modified. AONs comprising a backbone consisting of one form of (modified) internucleosidic linkages, multiple forms of (modified) internucleosidic linkages, uniformly or non-uniformly distributed along the length of the AON are all encompassed by the present invention. In addition, any modality of backbone modification (uniform, non-uniform, mono-form or pluriform and all permutations thereof) may be combined with any form or of sugar or nucleoside modifications or analogues mentioned below.

An especially preferred backbone for the AONs according to the invention is a uniform (all) phosphorothioate (PS) backbone. In another embodiment, a nucleotide analogue or equivalent of the invention comprises one or more base modifications or substitutions. Modified bases comprise synthetic and natural bases such as inosine, xanthine, hypoxanthine and other -aza, deaza, -hydroxy, -halo, -thio, thiol, -alkyl, -alkenyl, -alkynyl, thioalkyl derivatives of pyrimidine and purine bases that are or will be known in the art.

It is understood by a skilled person that it is not necessary for all positions in an AON to be modified uniformly. In addition, more than one of the aforementioned analogues or equivalents may be incorporated in a single AON or even at a single position within an AON. In certain embodiments, an AON of the invention has at least two different types of analogues or equivalents.

According to another embodiment AONs according to the invention comprise a 2'-O (preferably lower) alkyl phosphorothioate AON, such as 2'-O-methyl modified ribose (RNA), 2'-O-methoxyethyl modified ribose, 2'-O-ethyl modified ribose, 2'-O-propyl modified ribose, and/or substituted derivatives of these modifications such as halogenated derivatives.

An effective and preferred AON format according to the invention comprises 2'-O-methyl modified ribose moieties with a phosphorothioate backbone, preferably wherein substantially all ribose moieties are 2'-O-methyl and substantially all internucleosidic linkages are phosphorothioate linkages. It will also be understood by a skilled person that different AONs can be combined for efficiently skipping of exon 7 and/or exon 8 of the APP gene. A combination of two AONs may be used in a method of the invention, such as two AONs, three different AONs, four different AONs, or five different AONs targeting the same or different target regions of exon 7 and exon 8 (see FIG. 2), as long as at least one AON is one according to the invention. An AON can be linked to a moiety that enhances uptake of the AON in cells, preferably brain cells.

Examples of such moieties are cholesterols, carbohydrates, vitamins, biotin, lipids, phospholipids, cell-penetrating peptides including but not limited to antennapedia, TAT, transportan and positively charged amino acids such as oligoarginine, poly-arginine, oligolysine or polylysine, antigen-binding domains such as provided by an antibody, a Fab fragment of an antibody, or a single chain antigen binding domain such as a camelid single domain antigen-binding domain or a scFv.

An exon skipping AON according to the invention may be a naked (gymnotic) AON or in the form of a conjugate, a nanoparticle, or expressed from a vector (vectored AON). The exon skipping AON may be administrated using suitable means known in the art. When the exon skipping AON is a vectored AON, it may for example be provided to an individual or a cell, tissue or organ of said individual in the form of an expression vector wherein the expression vector encodes a transcript comprising said AON. The expression vector is preferably introduced into a cell, tissue, organ or individual via a gene delivery vehicle, such as a viral vector. In a preferred embodiment, there is provided a viral-based expression vector comprising an expression cassette or a transcription cassette that drives expression or transcription of an exon skipping AON as identified herein. Accordingly, the present invention provides a viral vector expressing an exon skipping AON according to the invention when placed under conditions conducive to expression of the exon skipping AON. A cell can be provided with an exon skipping AON capable of interfering with sequences essential for, or at least conducive to, exon 7 and/or exon 8 inclusion, such that such interference prevents, or at least reduces, exon 7/8 inclusion into the APP mRNA, for example by plasmid-derived AON expression or viral expression provided by adenovirus- or adeno-associated virus-based vectors. Expression may be driven by a polymerase III promoter, such as a Ul, a U6, or a U7 RNA promoter. A preferred delivery vehicle is a viral vector such as an adeno-associated virus vector (AAV), or a retroviral vector such as a lentivirus vector and the like. Also, plasmids, artificial chromosomes, plasmids usable for targeted homologous recombination and integration in the mammalian (preferably human) genome of cells may be suitably applied for delivery of an AON as defined herein. Preferred for the current invention are those vectors wherein transcription is driven from Pol-Ill promoters, and/or wherein transcripts are in the form of fusions with Ul or U7 transcripts, which yield good results for delivering small transcripts. It is within the skill of the artisan to design suitable transcripts. Preferred are Pol-Ill driven transcripts. Preferably, in the form of a fusion transcript with an Ul or U7 transcript. Such fusions may be generated as described in the art [33, 34].

One preferred AON expression system is an adenovirus associated virus (AAV)-based vector. Single chain and double chain AAV-based vectors have been developed that can be used for prolonged expression of AON sequences for highly efficient skipping of APP exon 17. A preferred AAV-based vector for instance comprises an expression cassette that is driven by a polymerase Ill-promoter (Pol III). A preferred Pol III promoter is, for 10) example, a Ul, a U6, or a U7 RNA promoter. The invention therefore also provides a viral-based vector, comprising a Pol Ill-promoter driven expression cassette for expression of an AON of the invention for inducing skipping of APP exon 7 and/or exon 8.

An AAV vector according to the present invention is a recombinant AAV vector and refers to an AAV vector comprising part of an AAV genome comprising an encoded exon skipping AON according to the invention encapsidated in a protein shell of capsid protein derived from an AAV serotype as depicted elsewhere herein. Part of an AAV genome may contain the inverted terminal repeats (ITR) derived from an adeno-associated virus serotype, such as AAV1, AAV2, AAV3, AAV4, AAV5, AAV8, AAV9 and others. Protein shell comprised of capsid protein may be derived from an AAV serotype such as AAV1, 2, 3, 4, 5, 8, 9 and others. A protein shell may also be named a capsid protein shell. AAV vector may have one or preferably all wild type AAV genes deleted, but may still comprise functional ITR nucleic acid sequences. Functional ITR sequences are necessary for the replication, rescue and packaging of AAV virions. The ITR sequences may be wild type sequences or may have at least 80%, 85%, 90%, 95, or 100% sequence identity with wild type sequences or may be altered by for example in insertion, mutation, deletion or substitution of nucleotides, as long as they remain functional. In this context, functionality refers to the ability to direct packaging of the genome into the capsid shell and then allow for expression in the host cell to be infected or target cell. In the context of the present invention a capsid protein shell may be of a different serotype than the AAV vector genome ITR. An AAV vector according to present the invention may thus be composed of a capsid protein shell, i.e. the icosahedral capsid, which comprises capsid proteins (VP1, VP2, and/or VP3) of one AAV serotype, e.g. AAV serotype 2, whereas the ITRs sequences contained in that AAV5 vector may be any of the AAV serotypes described above, including an AAV2 vector. An "AAV2 vector" thus comprises a capsid protein shell of AAV serotype 2, while e.g. an "AAV5 vector" comprises a capsid protein shell of AAV serotype 5, whereby either may encapsidate any AAV vector genome ITR according to the invention.

Preferably, a recombinant AAV vector according to the present invention comprises a capsid protein shell of AAV serotype 2, 5, 8 or AAV serotype 9 wherein the AAV genome or ITRs present in said AAV vector are derived from AAV serotype 2, 5, 8 or AAV serotype 9; such AAV vector is referred to as an AAV2/2, AAV 2/5, AAV2/8, AAV2/9, AAV5/2, AAV5/5, AAV5/8, AAV 5/9, AAV8/2, AAV 8/5, AAV8/8, AAV8/9, AAV9/2, AAV9/5, AAV9/8, or an AAV9/9 vector, respectively.

More preferably, a recombinant AAV vector according to the present invention has tropism for neuronal cells and comprises a capsid protein shell of AAV serotype, including serotypes 1, 2, 5, 7 and 8. The AAV genome or IT s present in said vector may be derived from the same or a different serotype, such as AAV serotype 2; such vector is referred to as, for example, an AAV 2/8 or AAV 2/9 vector.

More recently, AAV 9 has been reported to possess excellent tropism for neuronal cells in the primate brain [35]. Hence, the instant invention provides recombinant AAV vectors for delivering AON-expressing constructs to neuronal cells in the brain of AD patients, comprising serotypes 1, 2, 5, 7, 8 and 9, including chimeric rAAV vectors with similar tropism.

In order to improve specificity and reduce toxicity, cell-type specific promoters may be selected that favor, for example, neuronal expression over glial or oligodendrocyte expression.

Various methods of delivery, including intraventricular, intrathecal, intra-parenchymal, intranasal, as well as systemic, including intravenous, subcutaneous methods of delivery are contemplated by the instant invention. Particularly good results have been obtained in clinical studies where patients were dosed with AONs by intrathecal injections. Following intrathecal injection, AONs travel to the brain where they diffuse into various regions of the brain, followed by uptake by a wide variety of cell types.

One method that has been reported to enhance neuronal expression in adults is the use of mannitol to relax the blood-brain barrier to allow vector entry into the CNS [36].

A nucleic acid molecule encoding an exon skipping AON according to the present invention represented by a nucleic acid sequence of choice is preferably inserted between the AAV genome or ITR sequences as identified above, for example an expression construct comprising an expression regulatory element operably linked to a coding sequence and a 3' termination sequence. "AAV helper functions" generally refers to the corresponding AAV functions required for AAV replication and packaging supplied to the AAV vector in trans. AAV helper functions complement the AAV functions which are missing in the AAV vector, but they lack AAV ITRs (which are provided by the AAV vector genome). AAV helper functions include the two major ORFs of AAV, namely the rep coding region and the cap coding region or functional substantially identical sequences thereof. Rep and Cap regions are well known in the art [37]. The AAV helper functions can be supplied on an AAV helper construct, which may be a plasmid. Introduction of the helper construct into the host cell can occur e.g. by transformation, transfection, or transduction prior to or concurrently with the introduction of the AAV genome present in the AAV vector as identified herein. The AAV helper constructs of the invention may thus be chosen such that they produce the desired combination of serotypes for the AAV vector's capsid protein shell on the one hand and for the AAV genome present in said AAV vector replication and packaging on the other hand.

"AAV helper virus" provides additional functions required for AAV replication and packaging. Suitable AAV helper viruses include adenoviruses, herpes simplex viruses (such as HSV types 1 and 2) and vaccinia viruses. The additional functions provided by the helper virus can also be introduced into the host cell via vectors, as described in U.S. Pat. No. 6,531,456 (incorporated herein by reference). Preferably, an AAV genome as present in a recombinant AAV vector according to the present invention does not comprise any nucleotide sequences encoding viral proteins, such as the rep (replication) or cap (capsid) genes of AAV. An AAV genome may further comprise a marker or reporter gene, such as a gene for example encoding an antibiotic resistance gene, a fluorescent protein (e.g. gfp) or a gene encoding a chemically, enzymatically or otherwise detectable and/or selectable product (e.g. lacZ, aph, etc.) known in the art.

Gymnotic AONs in aqueous solution are readily taken up by most cells in vivo, and usually dissolving the AONs according to the invention in an isotonic (saline) solution will be sufficient to reach the target cells, such as neuronal cell in the human brain.

Alternatively, gymnotic AONs of the invention may be formulated using pharmaceutically acceptable excipients, additives, stabilizers and the like. Gymnotic AONs may also be formulated with any of the transfection aids mentioned below.

Skipping of exon 7, but not exon 8, occurs in vivo. However, referring to FIGS. 5A and 5B, in addition, a novel product corresponding to an APP mRNA including exon 8, but not exon 7, was surprisingly generated. This mRNA has not been previously described and it likely corresponds to a non-physiological variant, as it has not been found in vivo to date.

The nucleotide sequence of one embodiment of the novel APP mRNA which includes exon 8, but excludes exon 7, of the human amyloid precursor protein (APP) gene is 2145 nucleotides in length, and is provided herein as SEQ ID No: 21, as follows:

[SEQ ID No: 21]
ATGCTGCCCGGTTTGGCACTGCTCCTGCTGGCCGCCTGGACGGCTCGGG

CGCTGGAGGTACCCACTGATGGTAATGCTGGCCTGCTGGCTGAACCCCA

GATTGCCATGTTCTGTGGCAGACTGAACATGCACATGAATGTCCAGAAT

GGGAAGTGGGATTCAGATCCATCAGGGACCAAAACCTGCATTGATACCA

AGGAAGGCATCCTGCAGTATTGCCAAGAAGTCTACCCTGAACTGCAGAT

CACCAATGTGGTAGAAGCCAACCAACCAGTGACCATCCAGAACTGGTGC

AAGCGGGGCCGCAAGCAGTGCAAGACCCATCCCCACTTTGTGATTCCCT

ACCGCTGCTTAGTTGGTGAGTTTGTAAGTGATGCCCTTCTCGTTCCTGA

CAAGTGCAAATTCTTACACCAGGAGAGGATGGATGTTTGCGAAACTCAT

CTTCACTGGCACACCGTCGCCAAAGAGACATGCAGTGAGAAGAGTACCA

ACTTGCATGACTACGGCATGTTGCTGCCCTGCGGAATTGACAAGTTCCG

AGGGGTAGAGTTTGTGTGTTGCCCACTGGCTGAAGAAAGTGACAATGTG

GATTCTGCTGATGCGGAGGAGGATGACTCGGATGTCTGGTGGGCGGAG

CAGACACAGACTATGCAGATGGGAGTGAAGACAAAGTAGTAGAAGTAGC

AGAGGAGGAAGAAGTGGCTGAGGTGGAAGAAGAAGAAGCCGATGATGAC

GAGGACGATGAGGATGGTGATGAGGTAGAGGAAGAGGCTGAGGAACCCT

ACGAAGAAGCCACAGAGAGAACCACCAGCATTGCCACCACCACCACCAC

CACCACAGAGTCTGTGGAAGAGGTGGTTCGAGTGTCCCAAAGTTTACTC

AAGACTACCCAGGAACCTCTTGCCCGAGATCCTGTTAAACTTCCTACAA

CAGCAGCCAGTACCCCTGATGCCGTTGACAAGTATCTCGAGACACCTGG

GGATGAGAATGAACATGCCCATTTCCAGAAAGCCAAAGAGAGGCTTGAG

GCCAAGCACCGAGAGAGAATGTCCCAGGTCATGAGAGAATGGGAAGAGG

CAGAACGTCAAGCAAAGAACTTGCCTAAAGCTGATAAGAAGGCAGTTAT

```
-continued
CCAGCATTTCCAGGAGAAAGTGGAATCTTTGGAACAGGAAGCAGCCAAC

GAGAGACAGCAGCTGGTGGAGACACACATGGCCAGAGTGGAAGCCATGC

TCAATGACCGCCGCCGCCTGGCCCTGGAGAACTACATCACCGCTCTGCA

GGCTGTTCCTCCTCGGCCTCGTCACGTGTTCAATATGCTAAAGAAGTAT

GTCCGCGCAGAACAGAAGGACAGACAGCACACCCTAAAGCATTTCGAGC

ATGTGCGCATGGTGGATCCCAAGAAAGCCGCTCAGATCCGGTCCCAGGT

TATGACACACCTCCGTGTGATTTATGAGCGCATGAATCAGTCTCTCTCC

CTGCTCTACAACGTGCCTGCAGTGGCCGAGGAGATTCAGGATGAAGTTG

ATGAGCTGCTTCAGAAAGAGCAAAACTATTCAGATGACGTCTTGGCCAA

CATGATTAGTGAACCAAGGATCAGTTACGGAAACGATGCTCTCATGCCA

TCTTTGACCGAAACGAAAACCACCGTGGAGCTCCTTCCCGTGAATGGAG

AGTTCAGCCTGGACGATCTCCAGCCGTGGCATTCTTTTGGGGCTGACTC

TGTGCCAGCCAACACAGAAAACGAAGTTGAGCCTGTTGATGCCCGCCCT

GCTGCCGACCGAGGACTGACCACTCGACCAGGTTCTGGGTTGACAAATA

TCAAGACGGAGGAGATCTCTGAAGTGAAGATGGATGCAGAATTCCGACA

TGACTCAGGATATGAAGTTCATCATCAAAAATTGGTGTTCTTTGCAGAA

GATGTGGGTTCAAACAAAGGTGCAATCATTGGACTCATGGTGGGCGGTG

TTGTCATAGCGACAGTGATCGTCATCACCTTGGTGATGCTGAAGAAGAA

ACAGTACACATCCATTCATCATGGTGTGGTGGAGGTTGACGCCGCTGTC

ACCCCAGAGGAGCGCCACCTGTCCAAGATGCAGCAGAACGGCTACGAAA

ATCCAACCTACAAGTTCTTTGAGCAGATGCAGAACTAG
```

The peptide sequence encoded by one embodiment of the novel APP mRNA which includes exon 8, but excludes exon 7, of the human amyloid precursor protein (APP) gene is 714 amino acids in length, and is provided herein as SEQ ID No: 22, as follows:

```
                                        [SEQ ID No: 22]
MLPGLALLLLAAWTARALEVPTDGNAGLLAEPQIAMFCGRLNMHMNVQN

GKWDSDPSGTKTCIDTKEGILQYCQEVYPELQITNVVEANQPVTIQNWC

KRGRKQCKTHPHFVIPYRCLVGEFVSDALLVPDKCKFLHQERMDVCETH

LHWHTVAKETCSEKSTNLHDYGMLLPCGIDKFRGVEFVCCPLAEESDNV

DSADAEEDDSDVWWGGADTDYADGSEDKVVEVAEEEEVAEVEEEEADDD

EDDEDGDEVEEEAEEPYEEATERTTSIATTTTTTESVEEVVRVSQSLL

KTTQEPLARDPVKLPTTAASTPDAVDKYLETPGDENEHAHFQKAKERLE

AKHRERMSQVMREWEEAERQAKNLPKADKKAVIQHFQEKVESLEQEAAN

ERQQLVETHMARVEAMLNDRRRLALENYITALQAVPPRPRHVFNMLKKY

VRAEQKDRQHTLKHFEHVRMVDPKKAAQIRSQVMTHLRVIYERMNQSLS

LLYNVPAVAEEIQDEVDELLQKEQNYSDDVLANMISEPRISYGNDALMP

SLTETKTTVELLPVNGEFSLDDLQPWHSFGADSVPANTENEVEPVDARP

AADRGLTTRPGSGLTNIKTEEISEVKMDAEFRHDSGYEVHHQKLVFFAE

DVGSNKGAIIGLMVGGVVIATVIVITLVMLKKKQYTSIHHGVVEVDAAV

TPEERHLSKMQQNGYENPTYKFFEQMQN
```

Thus, according to another aspect of the invention, there is provided an isolated human APP polypeptide comprising an amino acid sequence substantially as set out in SEQ ID No: 22, or a variant or fragment thereof.

In a further aspect, there is provided an isolated human APP polypeptide comprising an amino acid sequence substantially as set out in SEQ ID No: 22, or a variant or fragment thereof, for use in therapy.

In yet another aspect, there is provided an isolated human APP polypeptide comprising an amino acid sequence substantially as set out in SEQ ID No: 22, or a variant or fragment thereof, for use in treating, preventing or ameliorating neurodegenerative disorder, preferably Alzheimer's disease.

The isolated human APP polypeptide is preferably encoded by a nucleotide sequence substantially as set out in SEQ ID No: 21, or a variant or fragment thereof.

It will be appreciated that the antisense oligonucleotide (AON) according to the invention may be used in a medicament which may be used in a monotherapy (i.e. use of the AON of the first aspect), for treating, ameliorating, or preventing neurodegenerative disorder, such as Alzheimer's disease. The inventors believe that targeting exon 7 for skipping may be enough to skip 8 as well. However, as discussed above, it is preferred that at least one AON for inducing exon 7 skipping is used in combination with at least one AON for inducing exon 8 skipping. Alternatively, the AON according to the invention may be used as an adjunct to, or in combination with, known therapies for treating, ameliorating, or preventing neurodegenerative disorders (e.g. Alzheimer's disease), such as other acetylcholinesterase inhibitors.

The AONs according to the invention may be combined in compositions having a number of different forms depending, in particular, on the manner in which the composition is to be used. Thus, for example, the composition may be in the form of a powder, tablet, capsule, liquid, ointment, cream, gel, hydrogel, aerosol, spray, micellar solution, transdermal patch, liposome suspension or any other suitable form that may be administered to a person or animal in need of treatment. It will be appreciated that the vehicle of medicaments according to the invention should be one which is well-tolerated by the subject to whom it is given, and preferably enables delivery of the AONs across the blood-brain barrier.

Medicaments comprising the AON according to the invention may be used in a number of ways. For instance, oral administration may be required, in which case the AON may be contained within a composition that may, for example, be ingested orally in the form of a tablet, capsule or liquid. An alternative option for administrating the AON would be to use a nasal spray, since administration by nasal spray reaches the brain faster and more efficiently than oral or intravenous ways of administration (see http://memory-zine.com/2010/07/26/nose-sprays-cross-blood-brain-barrier-faster-and-safer/). Hence, compositions comprising the AON of the invention may be administered by inhalation (e.g. intranasally). Compositions may also be formulated for topical use. For instance, creams or ointments may be applied to the skin, for example, adjacent to the brain.

The AON according to the invention may also be incorporated within a slow- or delayed-release device. Such devices may, for example, be inserted on or under the skin, and the medicament may be released over weeks or even months. The device may be located at least adjacent the treatment site, e.g. the head and brain. Such devices may be particularly advantageous when long-term treatment with the at least one antisense oligonucleotide (AON) according to the invention is required and which would normally require frequent administration (e.g. at least daily injection).

In another embodiment, intrathecal administration of the AON is preferred.

In a preferred embodiment, medicaments according to the invention may be administered to a subject by injection into the blood stream or directly into a site requiring treatment. For example, the medicament may be injected at least adjacent the brain. Injections may be intravenous (bolus or infusion) or subcutaneous (bolus or infusion), or intradermal (bolus or infusion).

It will be appreciated that the amount of the AON that is required is determined by its biological activity and bio-availability, which in turn depends on the mode of admin-istration, the physiochemical properties of the AON and whether it is being used as a monotherapy or in a combined therapy. The frequency of administration will also be influ-enced by the half-life of the AON within the subject being treated.

As described in Example 2, the inventors investigated the effective amounts of the AONs which can be used to cause exon skipping. As shown in FIG. 4, the inventors investi-gated effective dosages of one of the exon 7 skipping AONs (i.e. PMO 7.2) and one of the exon 8 skipping AONs (i.e. PMO 8.2).

Preferably, at least 50 nM, more preferably at least 100 nM, even more preferably at least 150 nM, and still more preferably at least 200 nM, and yet more preferably at least 250 nM of the AON causing exon 7 skipping is adminis-tered. Preferably, less than 3000 nM, more preferably less than 2000 nM, and still more preferably less than 1000 nM, and even more preferably less than 750 nM of the AON causing exon 7 skipping is administered. Preferably, the AON causing exon 7 skipping is SEQ ID No: 7 (PMO 7.2).

Preferably, at least 100 nM, more preferably at least 200 nM, even more preferably at least 300 nM, and still more preferably at least 400 nM, and yet more preferably at least 500 nM of the AON causing exon 8 skipping is adminis-tered. Preferably, less than 3000 nM, more preferably less than 2000 nM, and still more preferably less than 1000 nM, and even more preferably less than 750 nM of the AON causing exon 8 skipping is administered. Preferably, the AON causing exon 8 skipping is SEQ ID No: 13 (PMO 8.2). Preferably, at least 500 nM of each AON is administered.

Optimal dosages to be administered may be determined by those skilled in the art, and will vary with the particular AON in use, the strength of the pharmaceutical composition, the mode of administration, and the advancement of the neurodegenerative disease. Additional factors depending on the particular subject being treated will result in a need to adjust dosages, including subject age, weight, gender, diet, and time of administration.

Generally, a daily dose of between 0.001 μg/kg of body weight and 10 mg/kg of body weight of the AON according to the invention may be used for treating, ameliorating, or preventing neurodegenerative disease, depending upon which antisense oligonucleotide (AON) is used. More pref-erably, the daily dose is between 0.01 μg/kg of body weight and 1 mg/kg of body weight, and most preferably between approximately 0.1 μg/kg and 10 μg/kg body weight.

The AON may be administered before, during or after onset of neurodegenerative disease. Daily doses may be given as a single administration (e.g. a single daily injection or inhalation of a nasal spray). Alternatively, the AON may require administration twice or more times during a day. As an example, at least one antisense oligonucleotide (AON)

may be administered as two (or more depending upon the severity of the neurodegenerative disease being treated) daily doses of between 0.07 μg and 700 mg (i.e. assuming a body weight of 70 kg). A patient receiving treatment may take a first dose upon waking and then a second dose in the evening (if on a two dose regime) or at 3- or 4-hourly intervals thereafter. Alternatively, a slow release device may be used to provide optimal doses of antisense oligonucle-otide (AON) according to the invention to a patient without the need to administer repeated doses.

Known procedures, such as those conventionally employed by the pharmaceutical industry (e.g. in vivo experimentation, clinical trials, etc.), may be used to form specific formulations of the one or more AON according to the invention and precise therapeutic regimes (such as daily doses of the agents and the frequency of administration). The inventors believe that they are the first to suggest an anti-neurodegenerative disease composition, based on the use of the antisense oligonucleotides (AONs) of the inven-tion.

Hence, in an eighth aspect of the invention, there is provided a pharmaceutical composition comprising a thera-peutically effective amount of the antisense oligonucleotide (AON) according to the first aspect, and optionally a phar-maceutically acceptable vehicle.

The pharmaceutical composition is preferably an anti-neurodegenerative disease composition, i.e. a pharmaceuti-cal formulation used in the therapeutic amelioration, pre-vention or treatment of a neurodegenerative disorder in a subject, such as Alzheimer's disease.

The invention also provides in a ninth aspect, a process for making the pharmaceutical composition according to the eighth aspect, the process comprising combining a thera-peutically effective amount of the antisense oligonucleotide (AON) according to the first aspect, with a pharmaceutically acceptable vehicle.

In a particularly preferred embodiment, the AON is complementary to a target region within, or adjacent to, exon 7, and is selected from the group consisting of SEQ ID NO: 6, 7, 8, 9 and 10. In a particularly preferred embodiment, the AON is complementary to a target region within, or adjacent to, exon 8, and is selected from the group consisting of SEQ ID NO: 12, 13, 14 and 15. Preferably, the composition comprises one or more AON for causing exon 7 skipping in combination with one or more AON for causing exon 8 skipping. For example, preferably any one of the AON selected from the group consisting of SEQ ID NO: 6, 7, 8, 9 and 10, which have been shown to cause exon 7 skipping, may be used in combination with any one of the AON selected from the group consisting of SEQ ID NO: 12, 13, 14 or 15, which have been shown to cause exon 8 skipping. The most preferred exon 7 skipping AON is SEQ ID No: 7, and the most preferred exon 8 skipping AON is SEQ ID No: 13, and so these are most preferably used in combination with each other in the composition of the eighth aspect.

A "subject" may be a vertebrate, mammal, or domestic animal. Hence, medicaments according to the invention may be used to treat any mammal, for example livestock (e.g. a horse), pets, or may be used in other veterinary applications. Most preferably, however, the subject is a human being.

A "therapeutically effective amount" of AON is any amount which, when administered to a subject, is the amount of active agent that is needed to treat the neurode-generative disorder condition, or produce the desired effect.

For example, the therapeutically effective amount of AON used may be from about 0.001 mg to about 800 mg, and preferably from about 0.01 mg to about 500 mg. It is preferred that the amount of antisense oligonucleotide (AON) is an amount from about 0.1 mg to about 100 mg.

A "pharmaceutically acceptable vehicle" as referred to herein, is any known compound or combination of known compounds that are known to those skilled in the art to be useful in formulating pharmaceutical compositions.

In one embodiment, the pharmaceutically acceptable vehicle may be a solid, and the composition may be in the form of a powder or tablet. A solid pharmaceutically acceptable vehicle may include one or more substances which may also act as flavouring agents, lubricants, solubilisers, suspending agents, dyes, fillers, glidants, compression aids, inert binders, sweeteners, preservatives, coatings, or tablet-disintegrating agents. The vehicle may also be an encapsulating material. In powders, the vehicle is a finely divided solid that is in admixture with the finely divided active agents according to the invention. In tablets, the active agent (i.e. at least one antisense oligonucleotide (AON)) may be mixed with a vehicle having the necessary compression properties in suitable proportions and compacted in the shape and size desired. The powders and tablets preferably contain up to 99% of the active agents. Suitable solid vehicles include, for example calcium phosphate, magnesium stearate, talc, sugars, lactose, dextrin, starch, gelatin, cellulose, polyvinylpyrrolidine, low melting waxes and ion exchange resins. In another embodiment, the pharmaceutical vehicle may be a gel and the composition may be in the form of a cream or the like.

However, the pharmaceutical vehicle may be a liquid, and the pharmaceutical composition is in the form of a solution. Liquid vehicles are used in preparing solutions, suspensions, emulsions, syrups, elixirs and pressurized compositions. The active agent according to the invention (the AON) may be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilisers, emulsifiers, buffers, preservatives, sweeteners, flavouring agents, suspending agents, thickening agents, colours, viscosity regulators, stabilizers or osmo-regulators. Suitable examples of liquid vehicles for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the vehicle can also be an oily ester such as ethyl oleate and isopropyl myristate. Sterile liquid vehicles are useful in sterile liquid form compositions for parenteral administration. The liquid vehicle for pressurized compositions can be a halogenated hydrocarbon or other pharmaceutically acceptable propellant.

Liquid pharmaceutical compositions, which are sterile solutions or suspensions, can be utilized by, for example, intramuscular, intrathecal, epidural, intraperitoneal, intravenous and particularly subcutaneous injection. The one or more AON may be prepared as a sterile solid composition that may be dissolved or suspended at the time of administration using sterile water, saline, or other appropriate sterile injectable medium.

The at least one antisense oligonucleotide (AON) and compositions of the invention may be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like. The at least one antisense oligonucleotide (AON) used according to the invention can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

The inventors envisage the use genome editing tools, such as CRISPR, for modifying the target sequences described herein, as well as introducing insertions/deletions at splice acceptor and splice donor sites in order to mimic the results exhibited using the AONs described herein.

In another aspect, there is provided a method for making an internally truncated human APP protein lacking the region encoded by exon 7 and/or exon 8 in a human APP gene, the method comprising:

(i) deleting exon 7 and/or exon 8 from the endogenous APP coding sequence, (ii) replacing endogenous APP coding sequence with exogenous APP coding sequence which lacks exon 7 and/or exon 8, or (iii) modifying splice acceptor and/or splice donor sites corresponding to exon 7 and/or exon 8 in the endogenous APP coding sequence; and allowing the APP gene to be expressed, whereby an APP pre-mRNA is spliced by the splicing machinery of the cell, thereby producing mRNAs, wherein exon 7 and/or exon 8 is not included, and allowing said mRNA to be translated into the internally truncated human APP protein.

Preferably, the method comprises use of a genome editing technique, such CRISPR or homology-independent targeted integration (HITI). In one embodiment, CRISPR may be used to delete exons 7 and/or 8, preferably from neuronal cells. In another embodiment, HITI may be used to replace the endogenous APP gene with cDNA which lacks exons 7 and/or 8. In other words, a "knock-in" of a synthetic gene which lacks exons 7 and/or 8 is preferably performed. Alternatively, the method may comprise performing a knock-in of a mini gene into intron 6-7 that comprises a strong splice acceptor site followed by a cDNA of exons 9-18. This would bypass the transcription of exons 7 & 8, and thereby produce the 695cDNA. The method may be carried out in vivo, in vitro or ex vivo.

It will be appreciated that the invention extends to any nucleic acid or peptide or variant, derivative or analogue thereof, which comprises substantially the amino acid or nucleic acid sequences of any of the sequences referred to herein, including functional variants or functional fragments thereof. The terms "substantially the amino acid/nucleotide/peptide sequence", "functional variant" and "functional fragment", can be a sequence that has at least 40% sequence identity with the amino acid/nucleotide/peptide sequences of any one of the sequences referred to herein, for example 40% identity with the sequence identified herein, and so on.

Amino acid/polynucleotide/polypeptide sequences with a sequence identity which is greater than 65%, more preferably greater than 70%, even more preferably greater than 75%, and still more preferably greater than 80% sequence identity to any of the sequences referred to are also envisaged. Preferably, the amino acid/polynucleotide/polypeptide sequence has at least 85% identity with any of the sequences referred to, more preferably at least 90% identity, even more preferably at least 92% identity, even more preferably at least 95% identity, even more preferably at least 97% identity, even more preferably at least 98% identity and, most preferably at least 99% identity with any of the sequences referred to herein.

The skilled technician will appreciate how to calculate the percentage identity between two amino acid/polynucleotide/polypeptide sequences. In order to calculate the percentage identity between two amino acid/polynucleotide/polypeptide sequences, an alignment of the two sequences must first be prepared, followed by calculation of the sequence identity value. The percentage identity for two sequences may take different values depending on: (i) the method used to align the sequences, for example, ClustalW, BLAST, FASTA, Smith-Waterman (implemented in different programs), or structural alignment from 3D comparison; and (ii) the parameters used by the alignment method, for example, local vs global alignment, the pair-score matrix used (e.g. BLOSUM62, PAM250, Gonnet etc.), and gap-penalty, e.g. functional form and constants.

Having made the alignment, there are many different ways of calculating percentage identity between the two sequences. For example, one may divide the number of identities by: (i) the length of shortest sequence; (ii) the length of alignment; (iii) the mean length of sequence; (iv) the number of non-gap positions; or (iv) the number of equivalenced positions excluding overhangs. Furthermore, it will be appreciated that percentage identity is also strongly length dependent. Therefore, the shorter a pair of sequences is, the higher the sequence identity one may expect to occur by chance.

Hence, it will be appreciated that the accurate alignment of protein or DNA sequences is a complex process. The popular multiple alignment program ClustalW [38, 39] is a preferred way for generating multiple alignments of proteins or DNA in accordance with the invention. Suitable parameters for ClustalW may be as follows: For DNA alignments: Gap Open Penalty=15.0, Gap Extension Penalty=6.66, and Matrix=Identity. For protein alignments: Gap Open Penalty=10.0, Gap Extension Penalty=0.2, and Matrix=Gonnet. For DNA and Protein alignments: ENDGAP=−1, and GAP-DIST=4. Those skilled in the art will be aware that it may be necessary to vary these and other parameters for optimal sequence alignment.

Preferably, calculation of percentage identities between two amino acid/polynucleotide/polypeptide sequences may then be calculated from such an alignment as (N/T)*100, where N is the number of positions at which the sequences share an identical residue, and T is the total number of positions compared including gaps but excluding overhangs. Hence, a most preferred method for calculating percentage identity between two sequences comprises (i) preparing a sequence alignment using the ClustalW program using a suitable set of parameters, for example, as set out above; and (ii) inserting the values of N and T into the following formula:—Sequence Identity=(N/T)*100.

Alternative methods for identifying similar sequences will be known to those skilled in the art. For example, a substantially similar nucleotide sequence will be encoded by a sequence which hybridizes to DNA sequences or their complements under stringent conditions. By stringent conditions, we mean the nucleotide hybridises to filter-bound DNA or RNA in 3× sodium chloride/sodium citrate (SSC) at approximately 45° C. followed by at least one wash in 0.2× SSC/0.1% SDS at approximately 20-65° C. Alternatively, a substantially similar polypeptide may differ by at least 1, but less than 5, 10, 20, 50 or 100 amino acids from the sequences shown herein.

Due to the degeneracy of the genetic code, it is clear that any nucleic acid sequence described herein could be varied or changed without substantially affecting the sequence of the protein encoded thereby, to provide a functional variant thereof. Suitable nucleotide variants are those having a sequence altered by the substitution of different codons that encode the same amino acid within the sequence, thus producing a silent change. Other suitable variants are those having homologous nucleotide sequences but comprising all, or portions of, sequence, which are altered by the substitution of different codons that encode an amino acid with a side chain of similar biophysical properties to the amino acid it substitutes, to produce a conservative change. For example small non-polar, hydrophobic amino acids include glycine, alanine, leucine, isoleucine, valine, proline, and methionine. Large non-polar, hydrophobic amino acids include phenylalanine, tryptophan and tyrosine. The polar neutral amino acids include serine, threonine, cysteine, asparagine and glutamine. The positively charged (basic) amino acids include lysine, arginine and histidine. The negatively charged (acidic) amino acids include aspartic acid and glutamic acid. It will therefore be appreciated which amino acids may be replaced with an amino acid having similar biophysical properties, and the skilled technician will know the nucleotide sequences encoding these amino acids.

All of the features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying Figures, in which:—

BRIEF DESCRIPTION OF THE DRAWINGS

FIG. 3A shows an agarose gel illustrating the RT-PCR products of mRNAs isolated from non-transfected cells (Blank), cells transfected with a control PMO (E2) and cells transfected with 500 nM of PMOs 7.2, 8.2 and a combination of PMOs 7.2 and 8.2 (500 nM each).

EXAMPLES

Figure 1:
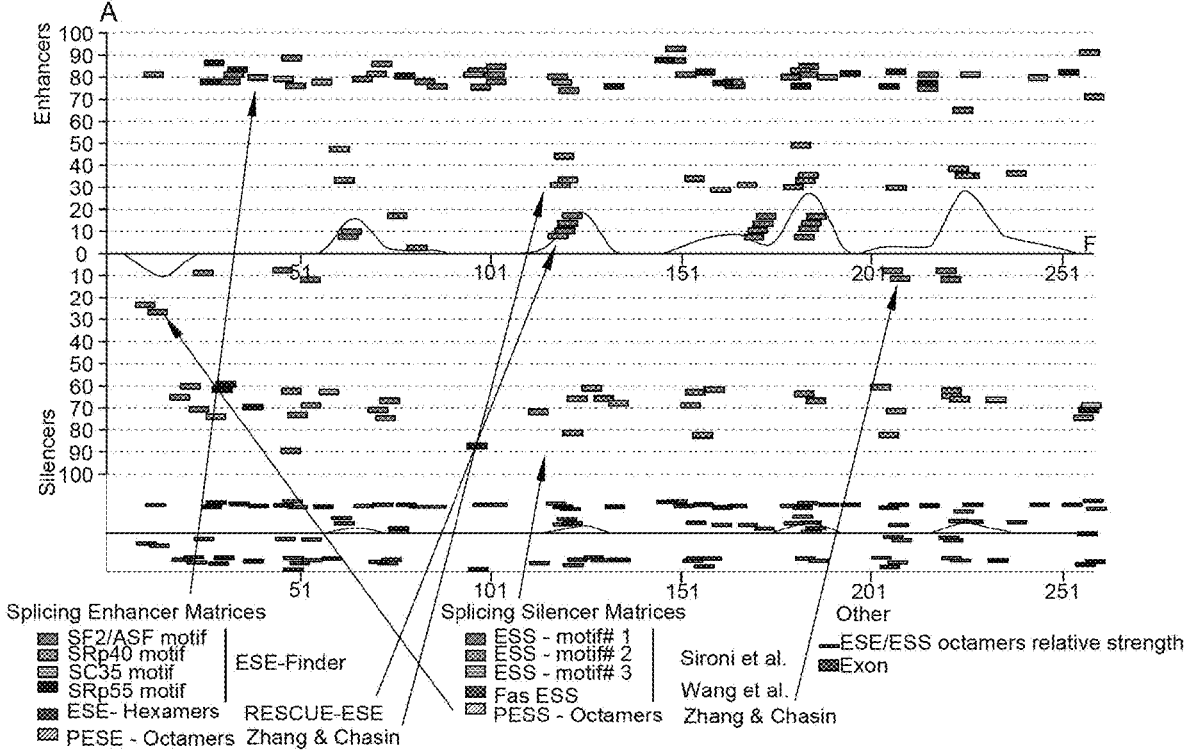
FIG. 1 shows a prediction of potential exonic splicing enhancers (ESEs) and exonic splicing silencers/suppressors (ESSs) for exon 7 (FIG. 1A) and exon 8 (FIG. 1B) using the Human Splicing Finder 2.4.
Figure 1:
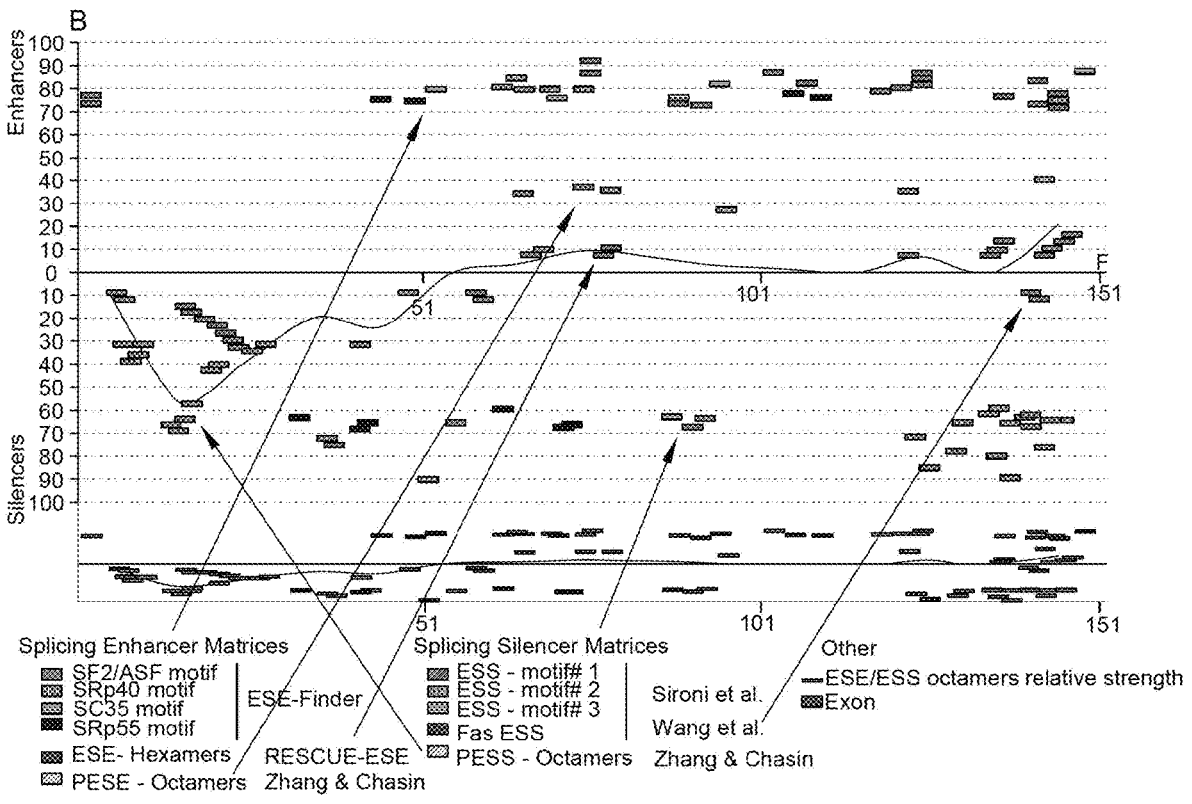

A significant contributor to the manifestation and progression of AD is the accumulation of amyloid beta produced by the proteolytic processing of APP. In the brain, three major transcripts of APP have been identified generated from alternative splicing either of exon 7 (APP751) or of exons 7 and 8 (APP695). Even though under physiological conditions, the predominant transcript in the brain is APP695, a significant increase in the levels of the longer transcripts (APP751 as well as the full length APP770 containing both exons 7 and 8) has been linked with the progression of AD. As described below, the inventors designed phosphorodiamidate morpholino antisense oligonucleotides (PMOs) to induce skipping of exons 7 and 8 and restore the non-disease associated splicing pattern of APP. The ability of several PMOs to induce exon skipping of exons 7 and 8 was tested in vitro in SH-SY5Y human neuroblastoma cells that express all three isoforms. The inventors have identified antisense oligonucleotides that efficiently reduce the inclusion of exons 7 and 8 from the mature mRNA that resulted in the increased expression of APP695 protein with an associated decrease in APP751 and APP770. This study demonstrates the feasibility of this exon skipping approach to alter APP splicing in AD.

Materials and Methods

Antisense Oligonucleotide (AON) Design

AONs were designed to exons 7 and 8 of the human APP gene using knowledge of putative SR protein binding motifs which are implicated in pre-mRNA splicing, as predicted by Human Splicing Finder 2.4.1 analysis of exon/intron sequences and secondary structure via MFold and calculations of the AON-target binding energies as predicted by Sfold [42]. For the analysis, the corresponding exons along with 50 nucleotides 3' and 5' of the exons were used. All AONs were synthesised as PMOs by GeneTools, LLC.

Cell Culture and Transfection

Human Neuroblastoma SH-SY5Y cells were grown in DMEM complete culture media—DMEM High Glucose (SIGMA) supplemented with 10% FBS (GIBCO), 1× Pen-Strep (GIBCO), 1× Non-Essential Amino Acids (SIGMA) and 1× GlutaMAX (GIBCO) and incubated at 37° C. with 5% CO2. The cells were seeded into 12 well plates in DMEM high glucose complete culture media for transfections. Undifferentiated cells were transfected with Endoporter/DMSO (Gene Tools) at a ratio of 6 ul of Endoporter per 1 ml of media according to manufacturer's instructions. PMO concentrations ranged from 50 nM to 1 μM.

RNA Extraction and RT-PCR

Cells were typically incubated for 24 hours post transfection before RNA was extracted by the RNeasy kit (Qiagen) as per the manufacturer's instruction. RNA was quantified on a nanodrop and 500 ng was used for a RT-PCR reaction with the GeneScript RT-PCR kit (Genesys) according to manufacturer's instructions. The primer sequences used were:

```
                                    (SEQ ID No: 16)
    fRT - GTGATGAGGTAGAGGAAGAGG, (SEQ ID No: 17)
    rRT - GTTGTAGAGCAGGGAGAGAG.
```

RT PCR conditions were: reverse transcription at 45° C. for 30 min, followed by: initial denaturation 92° C. for 2 min, 10 cycles of denaturation 92° C. for 30 s, annealing 62° C. for 30 s, extension 68° C. for 45 s, 25 cycles of denaturation 92° C. for 30 s, annealing 62° C. for 30 s, extension at 68° C. for 45 s+5 s/cycle, followed by final extension at 68° C. for 10 min, hold at 4° C. infinite.

A 1 μl aliquot of the RT-PCR product was used as template for a 30-cycle second round nested PCR reaction using 2× PCR Master Mix (Quantig Ltd.). Nested primer sequences used were:

```
                                    (SEQ ID No: 18)
    fNes - CACAGAGAGAACCACCAGCA, (SEQ ID No: 19)
    rNes - CTTGACGTTCTGCCTCTTCC.
```

Nester PCR conditions were: Initial denaturation 92° C. for 5 mins, 30 cycles denaturation 92° C. for 30 s, annealing 60° C. for 30 s, extension 68° C. for 45 s, followed by a final extension at 68° C. for 10 min, hold at 4° C. infinite.

PCR products were analysed on a 1% (w/v) agarose gel in TAE buffer and products were visualized with SyBr Safe. Exon skipping levels were determined by analysis of the PCR gels by densitometric analysis with Fiji image J [43].

Western Blotting

Protein samples were prepared by lysing SH-SY5Y cells 72 hrs after transfection, with RIPA buffer (150 mM NaCl, 10 mM EDTA, 50 mM HEPES, 1% (v/v) NP-40, 0.5% (w/v) Sodium Deoxycholate, 0.1% (w/v) SDS) with a protease inhibitor cocktail (Roche). Protein samples were prepared in 1× LDS sample buffer and 1× Reducing agent (Invitrogen) before being denatured at 75° C. for 8 minutes.

Samples were resolved on 10% (w/v) Tris-Glycine gels and transferred to an Amersham Protran 0.45 μM nitrocellulose membrane (GE Life Sciences). Membranes were blocked for 1 hour in TBS containing 0.05% (v/v) Tween-20, and 2.5% (w/v) dried milk powder. Membranes were then incubated with Anti-APP N terminal antibody MAb 348 (Sigma Aldrich) at a dilution of 1:1000 overnight at 4° C. in blocking buffer before being washed with TBS and then incubated with an anti-mouse IgG Dylight 680 secondary antibody (Cell Signalling) 1:5000 in TBS containing 2.5% dried milk powder (w/v). Detection was performed using Odyssey infrared imaging system from LI-COR biosciences and densitometric analysis was performed with Fiji Image J [43].

Modifying Expression of Neprilysin and APP 1) cDNA Synthesis

For each cDNA synthesis reaction, 0.5 μg random primers (Invitrogen), 0.5 μg Oligo (dT) (Promega) and 600 ng of RNA were added to a single tube, making up the volume to 10 μl with HyPure molecular grade water (LifeSciences). The reaction mixture was incubated at 70° C. for 5 minutes before being placed on ice. A master mix containing GoScript 5× buffer (Promega), GoScript enzyme (Promega), 2.5 mM MgCL2 (Promega), 0.5 mM dNTP (Promega), and HyPure molecular grade water (LifeSciences) made up to 15 ul was added to each reaction and run in a cDNA synthesis reaction. cDNA synthesis conditions were: annealing 25° C. 5 min, extension 42° C. 1 hour, inactivation of reverse transcriptase 70° C. 15 min, hold at 4° C. infinite. RNA from 3 biological replicates for each condition (7, 8, 7+8, E2, Blank) were used to perform this cDNA synthesis.

2) qPCR cDNA was diluted to required concentration and added to a well of a 384 well plate, followed by the required master mix being added. Master mixes consisted of 2× Light Cycler 480 Syber green I (Roche) and 0.5 μM appropriate primers (Sigma). Primer sequences are described below:

```
NEP:
                                    (SEQ ID No: 23)
F-CCTGGAGATTCATAATGGATCTTGT (SEQ ID No: 24)
R-AAAGGGCCTTGCGGAAAG
```

-continued

```
APP:
                                    (SEQ ID No: 25)
F-GATCCATCAGGGACCAAAAC (SEQ ID No: 26)
R-AGCGGTAGGGAATCACAAAG
```

Three biological replicates were used for each condition, and for each of these biological replicates, three technical replicates were performed.

The expression of at least one gene of interest and one housekeeping gene was studied in each experiment, and standards ranging from 1/20 to 1/2500 were used to allow for analysis of results. qPCR was run in a LightCycler480 qPCR machine (Roche). The PCR conditions were: pre-incubation 95° C. 5 min, 40 cycles of amplification 95° C. 15 sec, 60° C. sec, 72° C. 15 sec. qPCR was analysed using LightCycler480 software (Roche).

Example 1—Design of Antisense Oligonucleotides (AQNs)

Figure 2:
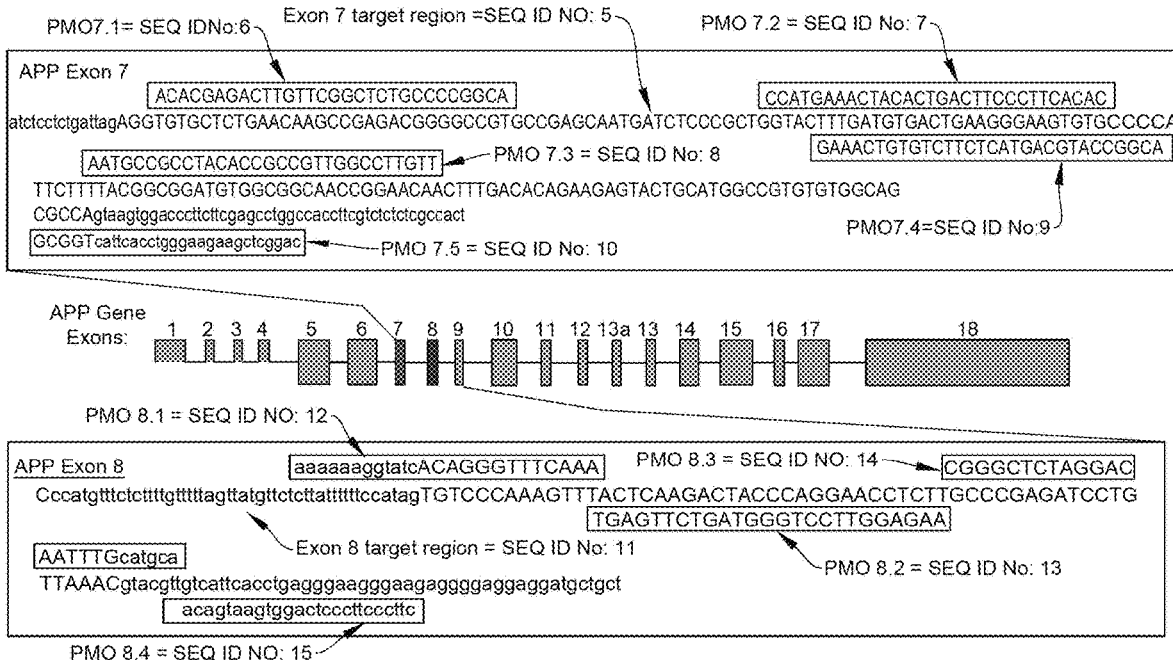
FIG. 2 shows an illustration of the genomic organization of the Amyloid Precursor Protein (APP) gene, and the localization of antisense oligonucleotides antisense oligonucleotides (AONs) in relation to the targeted exons 7 (SEQ ID No: 5) and 8 (SEQ ID No: 11). Exonic sequences are represented with capital letters, and intronic sequences are presented with small letters. Five sequences (PMO 7.1, 7.2, 7.3, 7.4 and 7.5) were chosen to target exon 7, and four sequences (PMO 8.1, 8.2, 8.3 and 8.4) were chosen for targeting exon 8. Phosphorodiamidate morpholino antisense oligonucleotides (i.e. PMO) sequences produced are shown in coloured boxes.

Since APP695 and APP751 isoforms are produced as a result of splicing out of exons 7 (APP751) or exons 7 and 8 (APP695), respectively, a unique set of AONs was designed to target these two exons. Referring first to FIG. 1, each exon sequence was analyzed for the presence of exonic splicing enhancers (ESEs) and exonic splicing suppressors or silencers (ESSs) using Human Splicing Finder 2.4.1. Referring to FIG. 2, to induce exon skipping, an AON was designed to specifically target ESEs, avoiding ESSs, if possible. Using the output from Human Splicing Finder 2.4.1, several 25 mer or 30 mer AONs targeting both exons were designed.

It has previously been established that a more efficacious AON would have its ends in open loop structures since this allows easier strand invasion and would bind to open conformation sequences more readily [44]. The predicted secondary structure of the pre-mRNA was therefore assessed for exon 7 and exon 8 using mfold and the binding sites of the designed AONs plotted.

Further to the open conformation of the target sequence, AONs that bind to their target more strongly are also predicted to be more efficacious [44]. Thermodynamic analysis of the binding of designed AONs to their target was performed using sfold and the results are summarised in Table 1.

TABLE 1

| A summary of the sequence and properties of the selected AONs | | | | | | | | | | |
|---|---|---|---|---|---|---|---|---|---|---|
| PMO name | Length | Target Exon | Target Sequence | PMO Sequence | GC Content of (%) | ΔG-Free energy of Exon | ΔG-Hairpin structure | ΔG-PMO-PMO | ΔG-Intermolecular Dimers | Total Binding energy |
| 7.1 | 30 bp | 7 | TGTGCTCTGAACAAG CCGAGACGGGGCCGT | ACGGCCCCGTCTCGGCTTG TTCAGAGCACA | 63.3 | −74.11 | −8.84 | −9.28 | −5.5 | −50.49 |
| 7.2 | 30 bp | 7 | GGTACTTTGATGTGA CTGAAGGGAAGTGTG | CACACTTCCCTTCAGTCAC ATCAAAGTACC | 46.7 | −74.11 | −1.82 | −4.88 | −6.5 | −60.91 |
| 7.3 | 30 bp | 7 | TTACGGCGGATGTGG CGGCAACCGGAACAA | TTGTTCCGGTTGCCGCCAC ATCCGCCGTAA | 60 | −74.11 | −4.85 | −9.75 | −2.7 | −56.81 |
| 7.4 | 30 bp | 7 | CTTTGACACAGAAGA GTACTGCATGGCCGT | ACGGCCATGCAGTACTCTT CTGTGTCAAAG | 50 | −74.11 | −5.37 | −9.28 | −9.6 | −49.86 |
| 7.5 | 30 bp | 7 | CGCCAgtaagtggac ccttcttcgagcctg | caggctcgaagaagggtcc acttacTGGCG | 60 | −74.11 | −7.3 | −6.76 | −8.5 | −51.55 |

TABLE 1-continued

A summary of the sequence and properties of the selected AONs

| PMO name | Length | Target Exon | Target Sequence | PMO Sequence | GC Content (%) | ΔG-Free energy of Exon | ΔG-Hairpin structure | ΔG-PMO-PMO | ΔG-Intermolecular Dimers | Total Binding energy |
|---|---|---|---|---|---|---|---|---|---|---|
| 8.1 | 25 bp | 8 | tttttccatagTGTCCCAAAGTTT | AAACTTTGGGACActatggaaaaaa | 32 | -30.09 | -4.48 | -3.89 | -4.6 | -17.12 |
| 8.2 | 25 bp | 8 | ACTCAAGACTACCCAGGAACCTCTT | AAGAGGTTCCTGGGTAGTCTTGAGT | 48 | -30.09 | -2.7 | -5.12 | -9.4 | -12.87 |
| 8.3 | 25 bp | 8 | GCCCGAGATCCTGTTAAACgtacgt | acgtacGTTTAACAGGATCTCGGGC | 48 | -30.09 | -2.95 | -13.55 | -9.8 | -3.79 |
| 8.4 | 25 bp | 8 | tgtcattcacctgagggaagggaag | cttcccttccctcaggtgaatgaca | 52 | -30.09 | -5.32 | -4.67 | -9.4 | -10.7 |

PMO 7.1 = SEQ ID No: 6
PMO 7.2 = SEQ ID No: 7
PMO 7.3 = SEQ ID No: 8
PMO 7.4 = SEQ ID No: 9
PMO 7.5 = SEQ ID No: 10
PMO 8.1 = SEQ ID No: 12
PMO 8.2 = SEQ ID No: 13
PMO 8.3 = SEQ ID No: 14
PMO 8.4 = SEQ ID No: 15

The overall analysis showed that all of the designed AONs target sequences rich in exonic splicing enhancers (ESE) motifs, have a high proportion of their target in open conformations, with all but one having at least one end in a predicted open loop structure and they all bind strongly to their target (see Table 1). Since PMO chemistries were used in this work, the % GC content (ideally 40-60%) for each AON designed, the length of any contiguous G stretches (less than 4), and the degree of self-complementarity (little or none) were also taken into consideration since these factors were believed to have a significant effect on synthesis yield, solubility and efficacy.

Example 2—Efficiency of PMOs Promoting Exclusion of Exons 7 & 8 in APP mRNA

The inventors next tested the activity of five PMOs targeting exon 7 and four PMOs targeting exon 8 by performing reverse transcription PCR (RT-PCR) of mRNA isolated from SH-SY5Y human neuroblastoma cells treated with each PMO at 500 nM for 48 hours. SH-SY5Y were used for this work due to their similarity to primary human neuronal cells and because they express all three neuronal APP mRNA variants [45].

Figure 3:
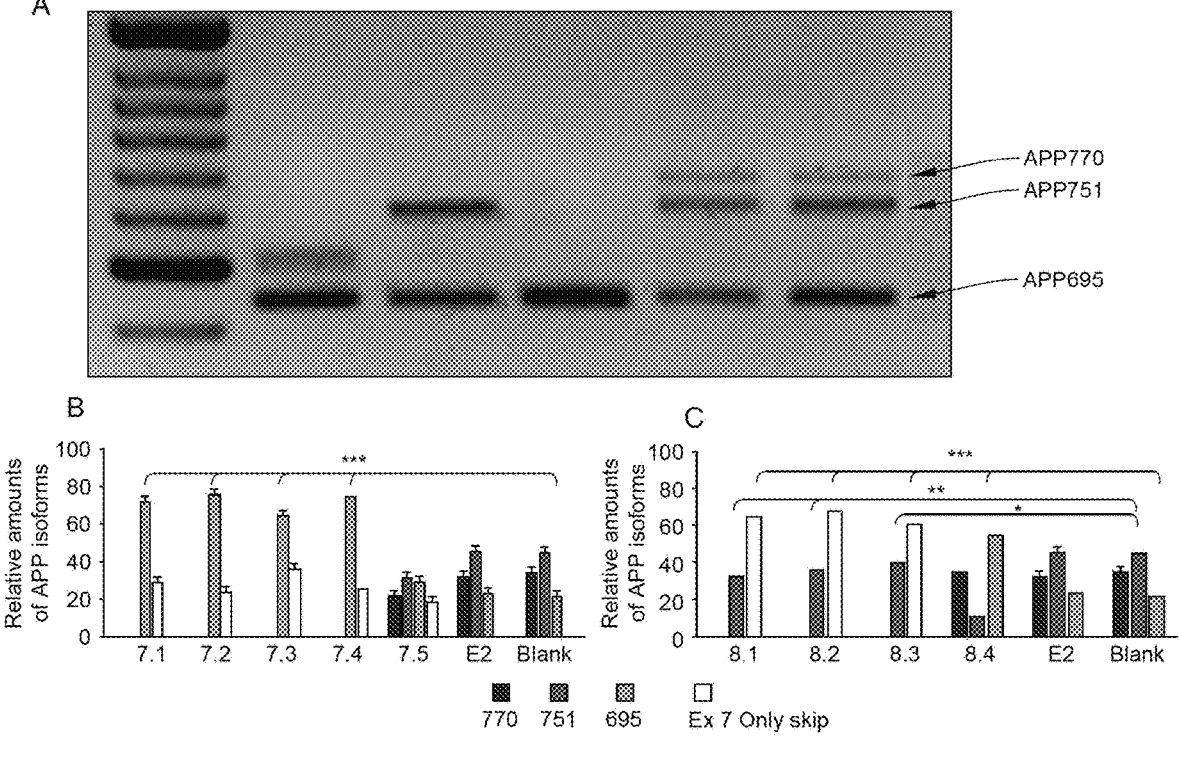
FIG. 3 (B)-(C) show the relative amount of each transcript was calculated as a ratio of the intensity of each PCR product over the intensity of all PCR products combined. (B) Transfection of 500 nM of PMOs 7.1, 7.2, 7.3 and 7.4 increased the relative expression of APP695 and promoted the exclusion of exon 7, whereas PMO 7.5 did not display significant activity. (C) Transfection of 500 nM of PMOs 8.1, 8.2 and 8.3 promoted the exclusion of exons 7 and 8 predominately from APP770 and less from APP751, increasing the relative amount of APP695, whereas PMO 8.4 promoted the exclusion of exon 8 only from APP751. n=3 independent experiments for all conditions. *p≤0.0001, p≤0.0014, *p≤0.0248, n=3 for all conditions.

First, the inventors examined the activity of PMOs targeting exon 7. Referring to FIG. 3A, transfection of SH-SY5Y cells with 500 nM of PMO was followed by a nested RT-PCR designed to detect the three variants of APP in one reaction. To quantitate the activity of the PMOs, the intensity of the characteristic band for each mRNA variant was measured using densitometry and was subsequently calculated as a percentage over the intensity of all PCR products. For consistency purposes, the cultures were renewed after 25-30 passages and each graph presented here is the average of three independent experiments performed in the same batch of cells. The relative amounts of the three isoforms were APP770: $34.1\pm3.3\%$, APP751: $44.6\pm0.9\%$ and APP695: $21.2\pm2.6\%$ for control (non-transfected) cells, and APP770: $31.8\pm2\%$, APP751: $45.4\pm1.2\%$ and APP695: $23.2\pm1.6\%$ for cells transfected with a control PMO (E2, targeting the human dystrophin gene). The sequence of this control PMO is CCAGCCCATCTTCTCCTGGTCCTGG (SEQ ID No: 20).

Referring to FIG. 3B, the results showed that PMOs 7.1, 7.2, 7.3 and 7.4, when used at 500 nM, significantly reduced the inclusion of exon 7 in the transcript increasing the amount of APP695 to $71.5\pm3.2\%$, $75.9\pm4.1\%$, $64.1\pm2.4\%$ and $74.7\pm0.1\%$, respectively, compared to control ($p\leq0.0001$, n=3). PMO 7.5 did not affect the splicing pattern of the mRNA of APP as much as the others, and the amount of APP695 was similar to control conditions ($28.6\pm4.6\%$, p=0.656, n=3).

Referring to FIGS. 3A and 3B, in addition, a novel product corresponding to an APP mRNA including exon 8 but not exon 7 was surprisingly generated. This mRNA has not been previously described and it likely corresponds to a non-physiological variant.

Next, the inventors examined the activity of four PMOs targeting exon 8 in SH-SY5Y cells transfected with 500 nM of each oligo. Referring to FIGS. 3A and 3C, the results showed that PMOs 8.1, 8.2 and 8.3 efficiently induced the exclusion of exon 8 and no detectable band corresponding to APP 770 could be detected. Quantification of the PCR products showed that the relative amount of APP751 was decreased for PMOs 8.1 and 8.2, but less so for PMO 8.3 ($31.9\pm0.3\%$, $35.8\pm0.2\%$ and $39.8\pm1.02\%$, respectively, compared to C: $44.6\pm0.9\%$. p=0.0014, 0.025 and p>0.05 respectively, n=3). Surprisingly, an increase in the relative levels of the shorter APP695 transcript was more prominent for PMOs 8.1, 8.2 and 8.3 ($64.1\pm0.3\%$, $68\pm0.2\%$ and $60\pm1.02\%$ respectively, compared to C: $21.2\pm2.6\%$. $p\leq0.0001$, n=3) suggesting a possible link between splicing of exon 7 with exon 8.

Similar to the other PMOs, PMO 8.4 increased the levels of APP695 ($54.7\pm0.01\%$ compared to C: $21.2\pm2.6\%$, $p\leq0.0001$, n=3) and reduced the relative amount of APP751 (APP751: $10.5\pm0.6\%$ compared to C: $44.6\pm0.9\%$, $p\leq0.0001$, n=3). Surprisingly, however, the relative expression of APP770 was not affected ($34.7\pm0.6\%$ compared to control $34.1\pm3.37$), suggesting that this PMO could only target APP751.

Figure 4:
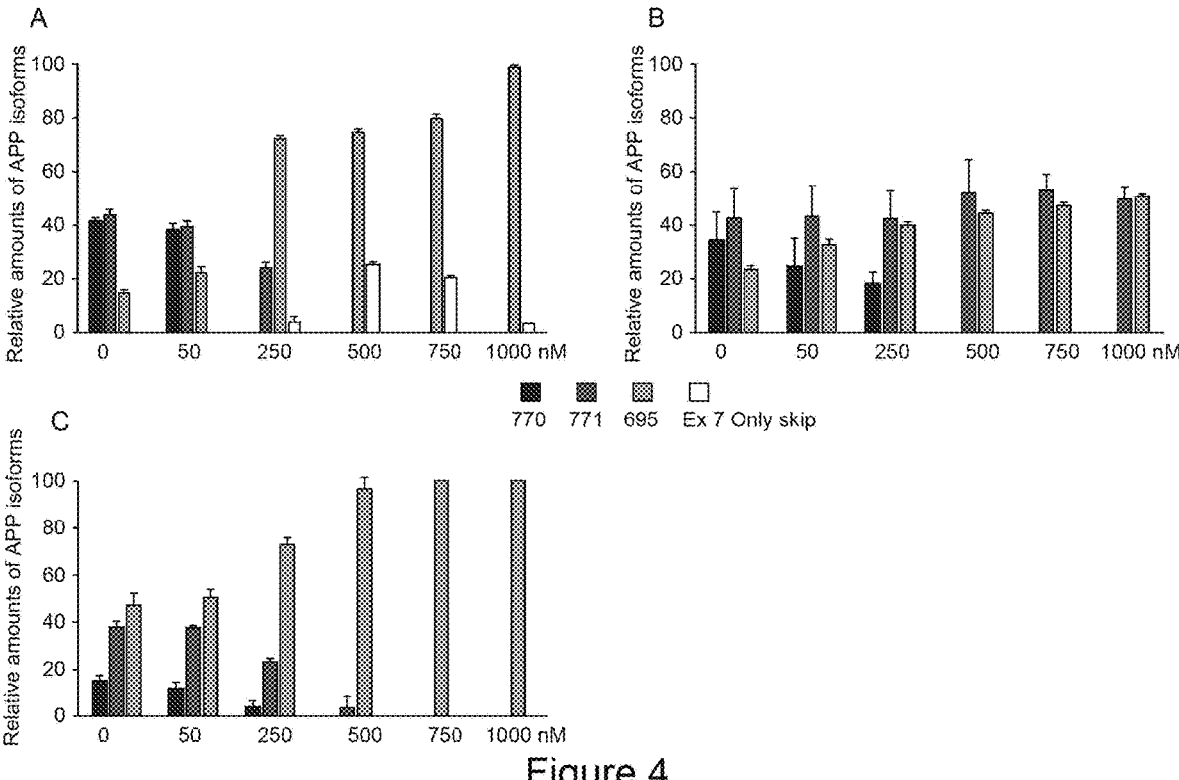
FIG. 4 shows the quantification of the relative amount of the different APP isoforms by RT-PCR from SH-SY5Y transfected with increasing amounts of PMOs 7.2, 8.2 and a combination of both. (A) Transfection of 250 nM of PMO 7.2 is sufficient to induce skipping of exon 7 from APP770 and 500 nM from both, APP770 and APP695. (B) Transfection of 500 nM of PMO 8.2 is sufficient to induce skipping of exon 7 and 8 from APP770 and increase the relative amount of APP 695. (C) Transfection of 7.2 and 8.2 effectively reduces the levels of APP770 and 751 at relatively low concentrations (500 nM each)

Having shown that the PMOs described herein can effectively induce skipping of the targeted exons 7 and 8, the inventors selected PMOs 7.2 and 8.2 and investigated in more detail their efficiency in promoting the exclusion of their target exons. To do so, SH-SY5Y cells were transfected with increasing concentrations of PMOs and RT-PCR of mRNA harvested from the transfected cells was performed to assess the extent of exon skipping, as shown in FIGS. 4A and 4B. First, with reference to FIG. 4A, the inventors calculated the relative amount of the full-length variant (APP770 that includes exon 7), in SH-SY5Y cells transfected with 50 nM, 250 nM, 500 nM, 750 nM and 1000 nM of PMO 7.2. The results showed that the expression of APP770 was similar between cells transfected with 50 nM of PMO oligo and control ($38.1\pm2.5\%$ and $41.3\pm1.4\%$, respectively), whereas transfection with 250 nM of PMO 7.2 or higher, was sufficient to completely abolish the inclusion of exon 7 from APP751. Interestingly, exon skipping of exon 7 from APP751 required higher concentrations of the PMO (500 nM). Finally, the inventors also noticed that at higher concentrations of the oligonucleotide (1 µM), exon 8 was also excluded, as shown in FIG. 4A, suggesting again a link between the splicing of exons 7 and 8.

Next, referring to FIG. 4B, the inventors assessed the efficiency of exon 8 exclusion by PMO 8.2. The results showed that complete skipping of exon 8 from APP770 was achieved with transfection of 500 nM of the oligonucleotide. Consistent to previous observations, the inventors noticed again a progressive increase of the relative amount of APP695 rather than the expected APP751 isoform ($32.6\pm2\%$, $39.8\pm1.2\%$, $44.1\pm1.2\%$, $47.2\pm0.9\%$ and $50.38\pm0.5\%$ with 50 nM, 250 nM, 500 nM, 750 nM and 1000 nM, respectively, for APP695 and $43.12\pm11.2\%$, $42.3\pm10.4\%$, $51.8\pm12.5\%$, $52.8\pm5.9\%$ and $49.6\pm4.2\%$ for 50 nM, 500 nM, 750 nM and 1000 nM respectively for APP751). These results suggest that the oligonucleotides that have been designed were efficiently inducing exon skipping of their targets, eliminating the inclusion of exons 7 and 8.

The inventors then went on to examine if a combination of both optimal antisense oligonucleotides, PMOs 7.2 and 8.2, would be effective in inducing the exclusion of both exons. To do so, SH-SY5Y cells were transfected with various concentrations of equimolar concentrations of a combination of PMOs 7.2 and 8.2 and compared the relative levels of APP variants by RT-PCR.

Referring to FIG. 4C, the results showed that the combination of both PMOs induced a concentration-dependent reduction of APP770 (from $14.8\pm2.7\%$ to $11.7\pm2.2\%$ at 50 nM, $3.9\pm3.4\%$ at 100 nM and 0 at higher concentrations) and APP751 (from $37.8\pm2.3\%$ to $37.5\pm1.1\%$ at 50 nM, $22.9\pm1.7\%$ at 100 nM, $3.5\pm4.9\%$ at 500 nM and 0 at higher concentrations) with a related increase in APP695 (from $47.3\pm5\%$ to $50.7\pm3.1\%$ at 50 nM, $73\pm2.8\%$ at 100 nM, $96.4\pm4.9\%$ at 500 nM and 100% at higher concentrations).

Example 3—Examination of Protein Concentrations Resulting from Exon Skipping Having shown that the PMOs that have been designed could effectively induce the skipping of their target exons at the mRNA level, the inventors then examined the protein levels produced by the three mRNA variants to ensure that the exon skipping events at the mRNA level could also be observed at the protein level. To do so, SH-SY5Y cells were transfected with 1 µM of PMO 7.2, PMO 8.2 and their combination for 72 h before lysing and their protein extracts were probed with an antibody detecting all variants of APP.

Figure 5:
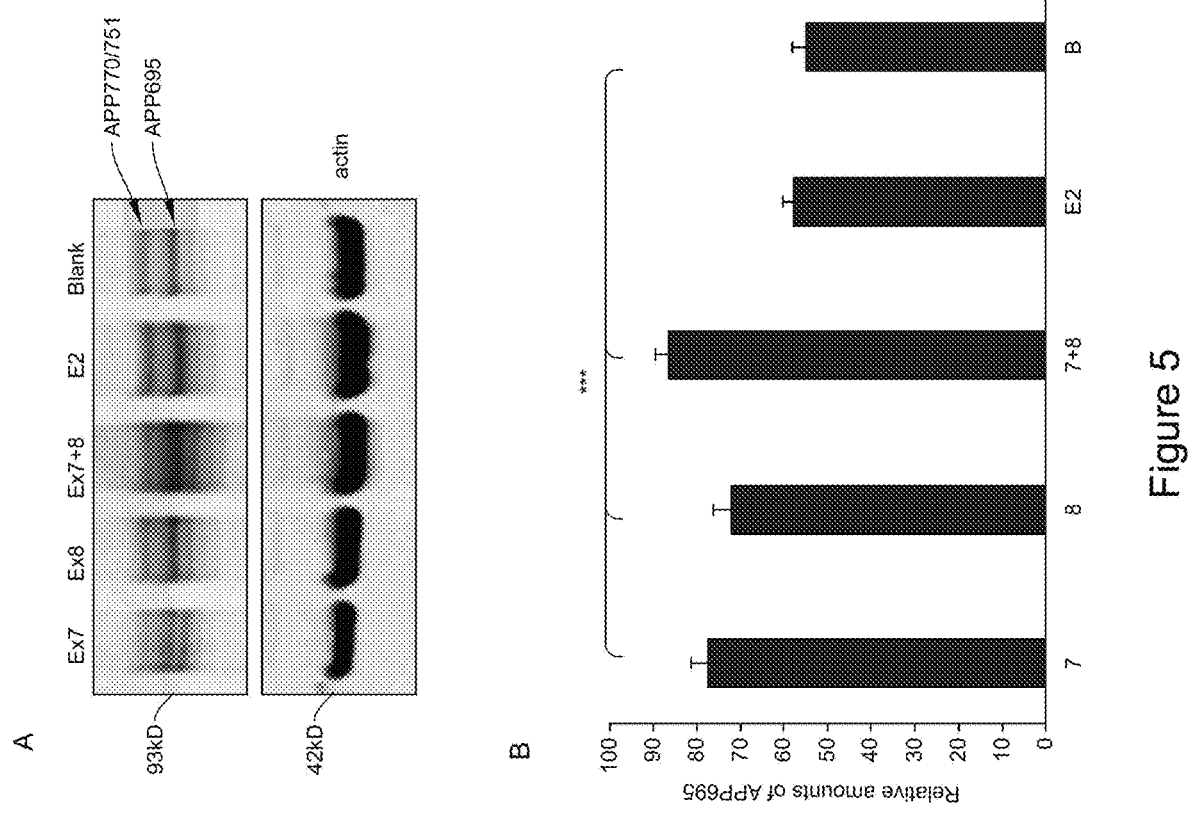
FIG. 5 (A) shows a representative image of a western blot illustrating the protein levels of APP from homogenates of non-transfected cells (Blank), cells transfected with a control PMO (E2) and cells transfected with 500 nM of PMOs 7.2, 8.2 and a combination of 7.2 and 8.2 (500 nM each). (B) The relative amount of APP695 calculated as a ratio of the intensity of APP695 over the intensity of all APP products showed a significant increase of APP695 in cells transfected with the designed PMOs. ***p=0.0001, n=3 for all conditions.
Figure 7:
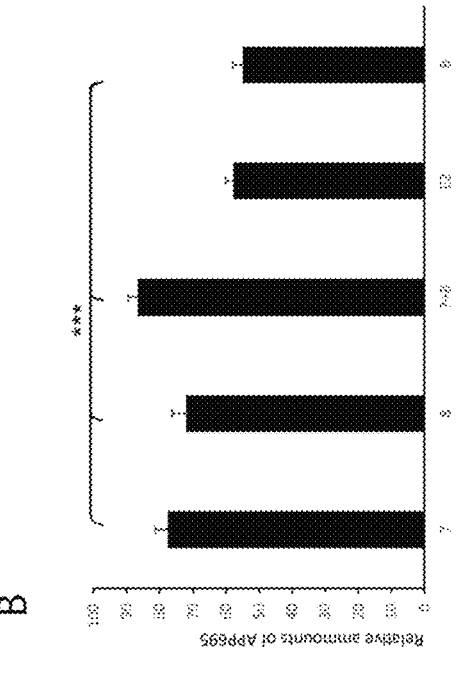
Figure 7:
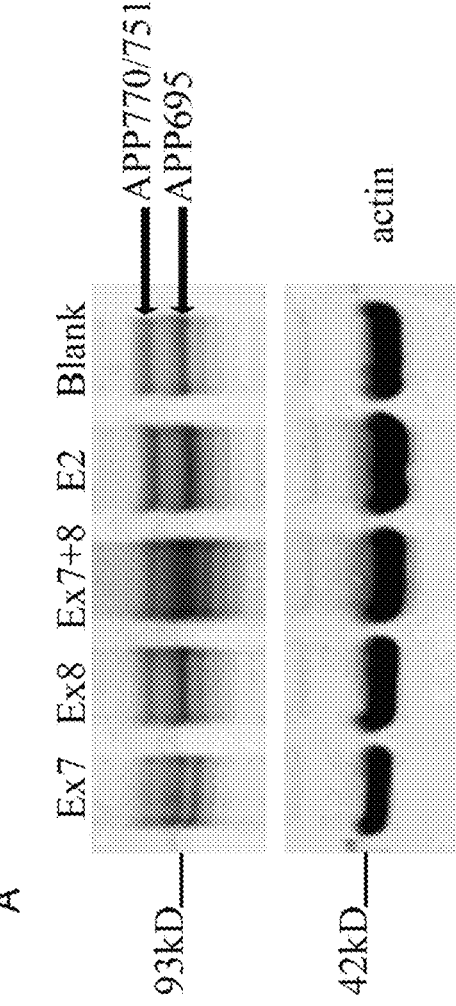
Figure 8:
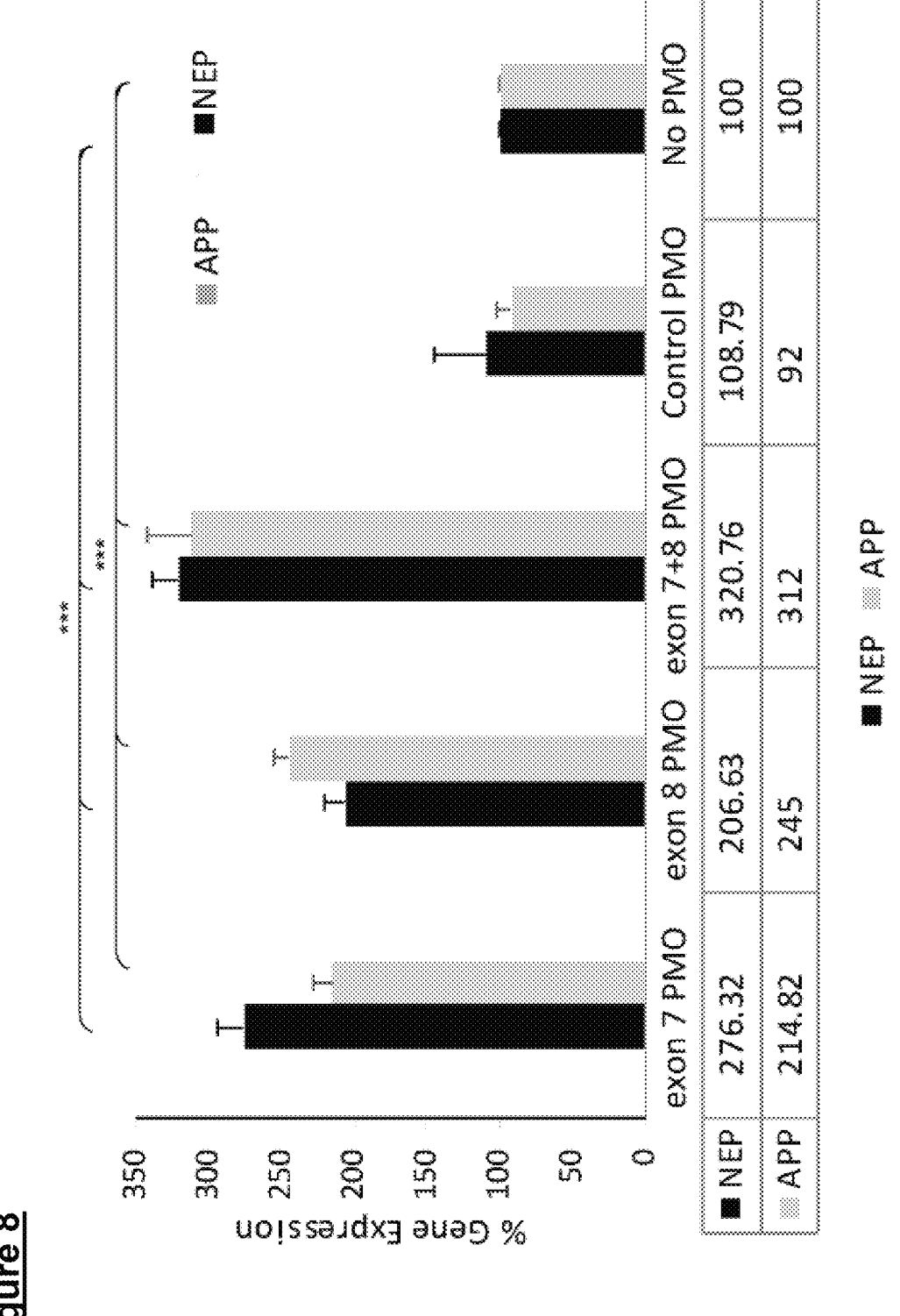

As shown in FIG. 5, APP770 and APP751 are very similar in size and could not be separated in the western blots (FIG. 7A) (FIG. 5A). They thus measured the relative amount of APP695 over total APP. Their results showed that the shift in APP695 that was detected from the RT-PCRs was also reflected at the protein level. The relative amount of APP695 in cells transfected with PMO 7.2 was significantly increased ($77.49\pm3.7\%$, p=0.0001, n=3) compared to control and E2 transfected cells ($57.7\pm2.5\%$ and $55\pm3\%$ respectively). Similarly, in cells transfected with PMO 8.2, the relative amount of APP695 was also increased ($72.1\pm4\%$, p=0.001, n=3) confirming the previous observations that at the mRNA level, skipping of exon 8 results in an increase of APP695 rather than APP751. Finally, in cells transfected with both PMOs, the relative amount of APP695 over total APP was $86.6\pm2.8\%$ (p=0.0001, n=3).

Example 4—Modifying Expression of Neprilysin and APP

Figure 6:
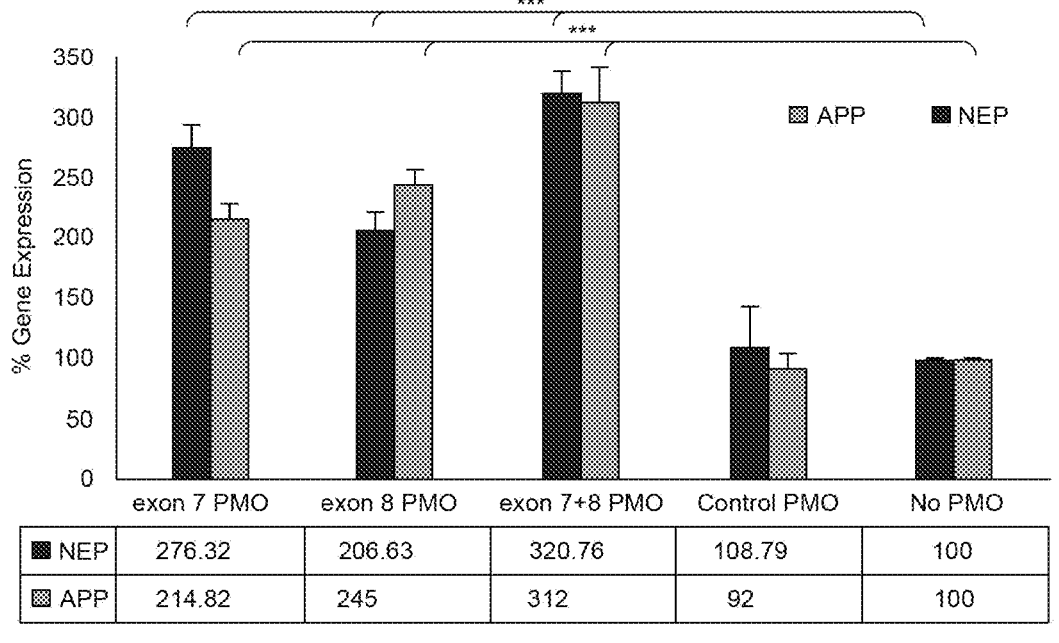
FIG. 6 shows gene expression levels of NEP by qPCR from SH-SY5Y neuroblastoma cells transfected with PMOs 7.2, 8.2 and a combination of both. Transfection of the PMOs enhances the expression levels of NEP compared to non-transfected cells, or cells transfected with a control PMO.

Referring to FIG. 6, the inventors went on to investigate the treatment of neuroblastoma cells with the designed PMOs, and demonstrated an increase in expression of two candidate marker genes, i.e. Neprilysin (NEP) and APP itself. Neprilysin is a zinc-dependent metalloprotease, which inactivates (i.e. cleaves) several peptides, including amyloid beta (AB). It has been suggested that its expression depends on APP695, the small isoform of APP that the inventors are attempting to enrich. Its connection to degrading amyloid beta shows how enriching for APP695 can benefit AD patients. Increase of APP expression has also been associated to APP695 and the results shown in FIG. 6 confirm that another transcriptional target of APP695 responds appropriately when the ratio is shifted. These results demonstrate that the predicted downstream effects are being exhibited by the influence of the PMOs described herein.

Example 5—CRISPR

The inventors envisage the use of the genome editing tool, CRISPR, for modifying the target sequences, as well as introducing insertions/deletions at splice acceptor and donor sites in order to mimic the results exhibited using the PMOs described herein. Furthermore, CRISPR can also be used to (i) try and delete both exons from neuronal cells, or (ii) replace the endogenous gene by a cDNA without exons 7 and 8, using homology-independent targeted integration (HITI). In other words, a "knock-in" of a synthetic gene which lacks exons 7 and 8 could be performed. Alternatively, it is possible to knock-in a mini gene into intron 6-7 that will have a strong splice acceptor site followed by a cDNA of exons 9-18. This would bypass the transcription of exons 7 & 8, and produce the 695cDNA.

Discussion

The results show that modified complementary oligonucleotides (i.e. the PMOs described herein) can be efficiently used to increase the expression of the APP695 mRNA variant in neuroblastoma cells. The primary goal was to design PMOs that would target two alternatively spliced exons of APP, i.e. exons 7 and 8. The inventors designed five PMOs targeting exon 7 and four PMOs targeting exon 8. Two of the designed PMOs were less active in inducing exon skipping of their targets than the others. Two of the most potent PMOs were selected, one for each exon (PMO 7.2 and PMO 8.2), and the inventors showed that it is possible to achieve 100% skipping of the targeted exons even at relatively low concentrations. Moreover, the inventors also showed that the abundancy of APP695 that was observed at the mRNA level was also apparent at the protein level when the optimal PMOs were used in combination.

These data clearly demonstrate that restoration of APP695 levels in vitro using PMOs is feasible, and so one can be optimistic of the implementation of the strategies described herein as a therapeutic approach to AD. In order to be able to use PMOs targeting the brain, significant amounts of PMOs have to be delivered in the brain. Although PMOs do not readily cross the blood brain barrier, several strategies have been described to deliver AONs to the brain overcoming the blood brain barrier that are yet to be tested in human subjects [46-48].

REFERENCES

1. Vuong, C. K., D. L. Black, and S. Zheng, *The neurogenetics of alternative splicing*. Nat Rev Neurosci, 2016. 17(5): p. 265-81.
2. Mills, J. D. and M. Janitz, *Alternative splicing of mRNA in the molecular pathology of neurodegenerative diseases*. Neurobiology of Aging, 2012. 33(5): p. 1012.e11-1012.e24.
3. Huang, Y. and L. Mucke, *Alzheimer mechanisms and therapeutic strategies*. Cell, 2012. 148(6): p. 1204-22.
4. Muller, U. C., T. Deller, and M. Korte, *Not just amyloid: physiological functions of the amyloid precursor protein family*. Nat Rev Neurosci, 2017. 18(5): p. 281-298.
5. Goldgaber, D., et al., *Characterization and chromosomal localization of a cDNA encoding brain amyloid of Alzheimer's disease*. Science, 1987. 235(4791): p. 877-80.
6. Tanzi, R. E., et al., *Amyloid beta protein gene: cDNA, mRNA distribution, and genetic linkage near the Alzheimer locus*. Science, 1987. 235(4791): p. 880-4.
7. Yoshikai, S., et al., *Genomic organization of the human amyloid beta-protein precursor gene*. Gene, 1990. 87(2): p. 257-63.
8. Kang, J., et al., *The precursor of Alzheimer's disease amyloid A4 protein resembles a cell-surface receptor*. Nature, 1987. 325(6106): p. 733-6.
9. Shariati, S. A. and B. De Strooper, *Redundancy and divergence in the amyloid precursor protein family*. FEBS Lett, 2013. 587(13): p. 2036-45.
10. Tanaka, S., et al., *Three types of amyloid protein precursor mRNA in human brain: their differential expression in Alzheimer's disease*. Biochem Biophys Res Commun, 1988. 157(2): p. 472-9.
11. Sandbrink, R., C. L. Masters, and K. Beyreuther, *APP gene family. Alternative splicing generates functionally related isoforms*. Ann N Y Acad Sci, 1996. 777: p. 281-7.
12. Weidemann, A., et al., *Identification, biogenesis, and localization of precursors of Alzheimer's disease A4 amyloid protein*. Cell, 1989. 57(1): p. 115-26.
13. Moir, R. D., et al., *Relative increase in Alzheimer's disease of soluble forms of cerebral Abeta amyloid protein precursor containing the Kunitz protease inhibitory domain*. J Biol Chem, 1998. 273(9): p. 5013-9.
14. Spillantini, M. G., et al., *Expression and cellular localization of amyloid beta-protein precursor transcripts in normal human brain and in Alzheimer's disease*. Brain Res Mol Brain Res, 1989. 6(2-3): p. 143-50.
15. Sandbrink, R., C. L. Masters, and K. Beyreuther, *APP gene family: unique age-associated changes in splicing of Alzheimer's betaA4-amyloid protein precursor*. Neurobiol Dis, 1994. 1(1-2): p. 13-24.
16. Zhan, S. S., et al., *APP with Kunitz type protease inhibitor domain (KPI) correlates with neuritic plaque density but not with cortical synaptophysin immunoreactivity in Alzheimer's disease and non-demented aged subjects: a multifactorial analysis*. Clin Neuropathol, 1995. 14(3): p. 142-9.
17. Willoughby, D. A., et al., *Beta-amyloid precursor protein (APP) and APP-RNA are rapidly affected by glutamate in cultured neurons: selective increase of mRNAs encoding a Kunitz protease inhibitor domain*. J Mol Neurosci, 1995. 6(4): p. 257-76.
18. Sandbrink, R., et al., *Expression of the APP gene family in brain cells, brain development and aging*. Gerontology, 1997. 43(1-2): p. 119-31.
19. Panegyres, P. K., *The effects of excitotoxicity on the expression of the amyloid precursor protein gene in the brain and its modulation by neuroprotective agents*. J Neural Transm (Vienna), 1998. 105(4-5): p. 463-78.
20. Matsui, T., et al., *Expression of APP pathway mRNAs and proteins in Alzheimer's disease*. Brain Res, 2007. 1161: p. 116-23.
21. Smith, P., et al., *In vivo regulation of amyloid precursor protein neuronal splicing by microRNAs*. Journal of Neurochemistry, 2011. 116(2): p. 240-247.
22. Bordji, K., et al., *Activation of Extrasynaptic, But Not Synaptic, NMDA Receptors Modifies Amyloid Precursor Protein Expression Pattern and Increases Amyloid-Production*. Journal of Neuroscience, 2010. 30(47): p. 15927-15942.
23. Palmert, M. R., et al., *The beta-amyloid protein precursor of Alzheimer disease has soluble derivatives found in human brain and cerebrospinal fluid*. Proc Natl Acad Sci USA, 1989. 86(16): p. 6338-42.
24. Hyman, B. T., et al., *Kunitz protease inhibitor-containing amyloid beta protein precursor immunoreactivity in Alzheimer's disease*. J Neuropathol Exp Neurol, 1992. 51(1): p. 76-83.
25. Belyaev, N. D., et al., *The transcriptionally active amyloid precursor protein(APP) intracellular domain is preferentially produced from the 695 isoform of APP in a {beta}-secretase-dependent pathway*. J Biol Chem, 2010. 285(53): p. 41443-54.
26. Ho, L., K. Fukuchi, and S. G. Younkin, *The alternatively spliced Kunitz protease inhibitor domain alters amyloid beta protein precursor processing and amyloid beta protein production in cultured cells*. J Biol Chem, 1996. 271(48): p. 30929-34.
27. Goodger, Z. V., et al., *Nuclear signaling by the APP intracellular domain occurs predominantly through the amyloidogenic processing pathway*. J Cell Sci, 2009. 122(Pt 20): p. 3703-14.
28. Flammang, B., et al., *Evidence that the amyloid-beta protein precursor intracellular domain, AICD, derives from beta-secretase-generated C-terminal fragment*. J Alzheimers Dis, 2012. 30(1): p. 145-53.
29. Nielsen, P. E., et al., *Sequence-selective recognition of DNA by strand displacement with a thymine-substituted polyamide*. Science, 1991. 254(5037): p. 1497-500.
30. Govindaraju, T. and V. A. Kumar, *Backbone-extended pyrrolidine peptide nucleic acids (bepPNA): design, synthesis and DNA/RNA binding studies*. Chem Commun (Camb), 2005(4): p. 495-7.

31. Egholm, M., et al., *PNA hybridizes to complementary oligonucleotides obeying the Watson-Crick hydrogen-bonding rules*. Nature, 1993. 365(6446): p. 566-8.

32. Morita, K., et al., *2'-O,4'-C-ethylene-bridged nucleic acids (ENA) with nuclease-resistance and high affinity for RNA*. Nucleic Acids Res Suppl, 2001(1): p. 241-2.

33. Gorman, L., et al., *Stable alteration of pre-mRNA splicing patterns by modified U7 small nuclear RNAs*. Proc Natl Acad Sci USA, 1998. 95(9): p. 4929-34.

34. Suter, D., et al., *Double-target antisense U7 snRNAs promote efficient skipping of an aberrant exon in three human beta-thalassemic mutations*. Hum Mol Genet, 1999. 8(13): p. 2415-23.

35. Dayton, R. D., D. B. Wang, and R. L. Klein, *The advent of AAV9 expands applications for brain and spinal cord gene delivery*. Expert Opin Biol Ther, 2012. 12(6): p. 757-66.

36. McCarty, D. M., et al., *Mannitol-facilitated CNS entry of rAAV2 vector significantly delayed the neurological disease progression in MPS IIIB mice*. Gene Ther, 2009. 16(11): p. 1340-52.

37. Chiorini, J. A., et al., *Cloning and characterization of adeno-associated virus type 5*. J Virol, 1999. 73(2): p. 1309-19.

38. Thompson, J. D., et al., *The CLUSTAL_X windows interface: flexible strategies for multiple sequence alignment aided by quality analysis tools*. Nucleic Acids Res, 1997. 25(24): p. 4876-82.

39. Thompson, J. D., D. G. Higgins, and T. J. Gibson, *CLUSTAL W: improving the sensitivity of progressive multiple sequence alignment through sequence weighting, position-specific gap penalties and weight matrix choice*. Nucleic Acids Res, 1994. 22(22): p. 4673-80.

40. Desmet, F. O., et al., *Human Splicing Finder: an online bioinformatics tool to predict splicing signals*. Nucleic Acids Res, 2009. 37(9): p. e67.

41. Zuker, M., *Mfold web server for nucleic acid folding and hybridization prediction*. Nucleic Acids Res, 2003. 31(13): p. 3406-15.

42. Ding, Y., C. Y. Chan, and C. E. Lawrence, *Sfold web server for statistical folding and rational design of nucleic acids*. Nucleic Acids Res, 2004. 32(Web Server issue): p. W135-41.

43. Schindelin, J., et al., *Fiji: an open-source platform for biological-image analysis*. Nat Methods, 2012. 9(7): p. 676-82.

44. Popplewell, L. J., et al., *Design of phosphorodiamidate morpholino oligomers(PMOs) for the induction of exon skipping of the human DMD gene*. Mol Ther, 2009. 17(3): p. 554-61.

45. Konig, G., C. L. Masters, and K. Beyreuther, *Retinoic acid induced differentiated neuroblastoma cells show increased expression of the beta A4 amyloid gene of Alzheimer's disease and an altered splicing pattern*. FEBS Lett, 1990. 269(2): p. 305-10.

46. Alvarez-Erviti, L., et al., *Delivery of siRNA to the mouse brain by systemic injection of targeted exosomes*. Nat Biotechnol, 2011. 29(4): p. 341-5.

47. Ding, H., et al., *Inhibition of brain tumor growth by intravenous poly(beta-L-malic acid) nanobioconjugate with pH-dependent drug release [corrected]*. Proc Natl Acad Sci USA, 2010. 107(42): p. 18143-8.

48. Rosi, N. L., et al., *Oligonucleotide-modified gold nanoparticles for intracellular gene regulation*. Science, 2006. 312(5776): p. 1027-30.

The invention claimed is:

1. An antisense oligonucleotide (AON) capable of reducing or preventing exon 7 and/or exon 8 inclusion into an amyloid precursor protein (APP) mRNA produced by splicing from an APP transcript wherein the AON comprises internucleosidic linkages which are chemically modified or wherein the AON comprises a phosphorodiamidate morpholino oligomer (PMO) and wherein the AON comprises a nucleotide sequence selected from the group consisting of SEQ ID Nos: 6, 7, 8, 9, 10, 12, 13, 14 and 15.

2. A pharmaceutical composition comprising a therapeutically effective amount of one or more AON according to claim 1.

3. A method of treating or ameliorating a neurodegenerative disorder in a subject, the method comprising: administering to a subject in need of such treatment, a therapeutically effective amount of one or more AON according to claim 1.

4. An antisense oligonucleotide (AON) capable of reducing or preventing exon 7 and/or exon 8 inclusion into an amyloid precursor protein (APP) mRNA produced by splicing from an APP transcript wherein the AON comprises internucleosidic linkages which are chemically modified or wherein the AON comprises a phosphorodiamidate morpholino oligomer (PMO) wherein a protein made by skipping exon 7 and 8 comprises the following features:

1) Exon 6 is joined with exon 9, maintaining the reading frame and resulting in a protein with 695 amino acids;

2) the Kunitz-type protease inhibitor domain (KPI), which is within exon 7, is removed; and/or 3) a domain sharing homology with the OX-2 antigen of thymus-derived lymphoid cells, which is within exon 8, is removed.

5. An AON according to claim 1, wherein the AON is capable of binding to and/or is complementary to a target region within:

(i) the 3' part of intron 6-7 and/or the 5' part of exon 7 of the APP gene;

(ii) exon 7 of the APP gene;

(iii) the 3' part of exon 7 and/or the 5' part of intron 7-8 of the APP gene;

(iv) the 3' part of intron 7-8 and/or the 5' part of exon 8 of the APP gene;

(v) exon 8 of the APP gene; and/or (vi) the 3' part of exon 8 and/or the 5' part of intron 8-9 of the APP gene.

6. An AON according to claim 5, wherein the AON is complementary to at least 8 nucleotides in the target region, or from 8 to 50 nucleotides, or from 12 to 50 nucleotides, in the target region, or wherein the AON has a length of from 18 to 42 nucleotides, or from 22 to 42, or from 27 to 39 nucleotides.

7. An AON according to claim 1, wherein when the AON is capable of reducing or preventing exon 7 inclusion into an APP mRNA produced by splicing from an APP transcript, the target region for the AON is between 150 nucleotides upstream of the intron 6/exon 7 junction (−150) and 150 nucleotides downstream of the exon 7/intron 7 junction (+150).

8. An AON according to claim 1, wherein the AON target region spans 15 nucleotides upstream and 150 nucleotides downstream of exon 7 of the human APP gene (−15 to +50), and is represented as SEQ ID NO: 5.

9. An AON according to claim 1, wherein when the AON is capable of reducing or preventing exon 8 inclusion into an APP mRNA produced by splicing from an APP transcript, the target region for the AON is between 150 nucleotides upstream of the intron 7/exon 8 junction (−150) and 150 nucleotides downstream of the exon 8/intron 8 junction (+150).

10. An AON according to claim 1, wherein the AON is complementary to a target region within, or adjacent to, exon 8, and comprises a nucleotide sequence selected from the group consisting of SEQ ID NO: 12, 13, 14 and 15.

11. A method according to claim 3 wherein the neurodegenerative disease is Alzheimer's disease.

12. A method according to claim 11, wherein one or more AON for causing exon 7 skipping is used in combination with one or more AON for causing exon 8 skipping, and wherein any one of the AON selected from the group consisting of SEQ ID NO: 6, 7, 8, 9 and 10 is used in combination with any one of the AON selected from the group consisting of SEQ ID NO: 12, 13, 14 or 15.

13. A method according to claim 3, wherein one or more AON for causing exon 7 skipping is used in combination with one or more AON for causing exon 8 skipping, and wherein any one of the AON is selected from the group consisting of SEQ ID NO: 6, 7, 8, 9 and 10 is used in combination with any one of the AON selected from the group consisting of SEQ ID NO: 12 13, 14 or 15.

14. The pharmaceutical composition of claim 2 comprising a pharmaceutically acceptable vehicle.

\* \* \* \* \*

SEQUENCE LISTING

```
Sequence total quantity: 28
SEQ ID NO: 1              moltype = DNA  length = 168
FEATURE                   Location/Qualifiers
source                    1..168
                          mol_type = other DNA
                          organism = Homo sapiens
SEQUENCE: 1
aggtgtgctc tgaacaagcc gagacggggc cgtgccgagc aatgatctcc cgctggtact   60
ttgatgtgac tgaagggaag tgtgccccat tcttttacgg cggatgtggc ggcaaccgga  120
acaactttga cacagaagag tactgcatgg ccgtgtgtgg cagcgcca                168

SEQ ID NO: 2              moltype = AA  length = 57
FEATURE                   Location/Qualifiers
source                    1..57
                          mol_type = protein
                          organism = Homo sapiens
SEQUENCE: 2
EVCSEQAETG PCRAMISRWY FDVTEGKCAP FFYGGCGGNR NNFDTEEYCM AVCGSAM         57

SEQ ID NO: 3              moltype = DNA  length = 57
FEATURE                   Location/Qualifiers
source                    1..57
                          mol_type = other DNA
                          organism = Homo sapiens
SEQUENCE: 3
tgtcccaaag tttactcaag actacccagg aacctcttgc ccgagatcct gttaaac         57

SEQ ID NO: 4              moltype = AA  length = 20
FEATURE                   Location/Qualifiers
source                    1..20
                          mol_type = protein
                          organism = Homo sapiens
SEQUENCE: 4
MSQSLLKTTQ EPLARDPVKL                                                  20

SEQ ID NO: 5              moltype = DNA  length = 233
```

-continued

```
FEATURE              Location/Qualifiers
misc_feature         1..233
                     note = Exon 7 target squence
source               1..233
                     mol_type = other DNA
                     organism = synthetic construct
SEQUENCE: 5
atctcctctg attagaggtg tgctctgaac aagccgagac ggggccgtgc cgagcaatga   60
tctcccgctg gtactttgat gtgactgaag ggaagtgtgc cccattcttt tacggcggat  120
gtggcggcaa ccggaacaac tttgacacag aagagtactg catggccgtg tgtggcagcg  180
ccagtaagtg gacccttctt cgagcctggc cacctttcgt ctctctcgcc act         233

SEQ ID NO: 6         moltype = DNA  length = 30
FEATURE              Location/Qualifiers
misc_feature         1..30
                     note = PMO 7.1
source               1..30
                     mol_type = other DNA
                     organism = synthetic construct
SEQUENCE: 6
acggccccgt ctcggcttgt tcagagcaca                                    30

SEQ ID NO: 7         moltype = DNA  length = 30
FEATURE              Location/Qualifiers
misc_feature         1..30
                     note = PMO 7.2
source               1..30
                     mol_type = other DNA
                     organism = synthetic construct
SEQUENCE: 7
cacacttccc ttcagtcaca tcaaagtacc                                    30

SEQ ID NO: 8         moltype = DNA  length = 30
FEATURE              Location/Qualifiers
misc_feature         1..30
                     note = PMO 7.4
source               1..30
                     mol_type = other DNA
                     organism = synthetic construct
SEQUENCE: 8
ttgttccggt tgccgccaca tccgccgtaa                                    30

SEQ ID NO: 9         moltype = DNA  length = 30
FEATURE              Location/Qualifiers
misc_feature         1..30
                     note = PMO 7.4
source               1..30
                     mol_type = other DNA
                     organism = synthetic construct
SEQUENCE: 9
acggccatgc agtactcttc tgtgtcaaag                                    30

SEQ ID NO: 10        moltype = DNA  length = 30
FEATURE              Location/Qualifiers
misc_feature         1..30
                     note = PMO 7.5
source               1..30
                     mol_type = other DNA
                     organism = synthetic construct
SEQUENCE: 10
caggctcgaa gaagggtcca cttactggcg                                    30

SEQ ID NO: 11        moltype = DNA  length = 157
FEATURE              Location/Qualifiers
misc_feature         1..157
                     note = AON target region of Exon 8 of App gene
source               1..157
                     mol_type = other DNA
                     organism = synthetic construct
SEQUENCE: 11
cccatgtttc tctttttgtt tttagttatg ttctcttatt ttttccatag tgtcccaaag   60
tttactcaag actacccagg aacctcttgc ccgagatcct gttaaacgta cgttgtcatt  120
cacctgaggg aagggaagag gggaggagga tgctgct                           157

SEQ ID NO: 12        moltype = DNA  length = 25
FEATURE              Location/Qualifiers
misc_feature         1..25
                     note = PMO 8.1
source               1..25
```

-continued

```
                         mol_type = other DNA
                         organism = synthetic construct
SEQUENCE: 12
aaactttggg acactatgga aaaaa                                              25

SEQ ID NO: 13           moltype = DNA   length = 25
FEATURE                 Location/Qualifiers
misc_feature            1..25
                        note = PMO 8.2
source                  1..25
                        mol_type = other DNA
                        organism = synthetic construct
SEQUENCE: 13
aagaggttcc tgggtagtct tgagt                                             25

SEQ ID NO: 14           moltype = DNA   length = 25
FEATURE                 Location/Qualifiers
misc_feature            1..25
                        note = PMO 8.3
source                  1..25
                        mol_type = other DNA
                        organism = synthetic construct
SEQUENCE: 14
acgtacgttt aacaggatct cgggc                                             25

SEQ ID NO: 15           moltype = DNA   length = 25
FEATURE                 Location/Qualifiers
misc_feature            1..25
                        note = PMO 8.4
source                  1..25
                        mol_type = other DNA
                        organism = synthetic construct
SEQUENCE: 15
cttcccttcc ctcaggtgaa tgaca                                             25

SEQ ID NO: 16           moltype = DNA   length = 21
FEATURE                 Location/Qualifiers
misc_feature            1..21
                        note = fRT primer
source                  1..21
                        mol_type = other DNA
                        organism = synthetic construct
SEQUENCE: 16
gtgatgaggt agaggaagag g                                                 21

SEQ ID NO: 17           moltype = DNA   length = 20
FEATURE                 Location/Qualifiers
misc_feature            1..20
                        note = rRT primer
source                  1..20
                        mol_type = other DNA
                        organism = synthetic construct
SEQUENCE: 17
gttgtagagc agggagagag                                                   20

SEQ ID NO: 18           moltype = DNA   length = 20
FEATURE                 Location/Qualifiers
misc_feature            1..20
                        note = fNes primer
source                  1..20
                        mol_type = other DNA
                        organism = synthetic construct
SEQUENCE: 18
cacagagaga accaccagca                                                   20

SEQ ID NO: 19           moltype = DNA   length = 20
FEATURE                 Location/Qualifiers
misc_feature            1..20
                        note = rNes primer
source                  1..20
                        mol_type = other DNA
                        organism = synthetic construct
SEQUENCE: 19
cttgacgttc tgcctcttcc                                                   20

SEQ ID NO: 20           moltype = DNA   length = 25
FEATURE                 Location/Qualifiers
misc_feature            1..25
                        note = Control PMO
```

-continued

```
source                1..25
                      mol_type = other DNA
                      organism = synthetic construct
SEQUENCE: 20
ccagcccatc ttctcctggt cctgg                                      25

SEQ ID NO: 21         moltype = DNA  length = 2145
FEATURE               Location/Qualifiers
misc_feature          1..2145
                      note = novel APP mRNA
source                1..2145
                      mol_type = other DNA
                      organism = synthetic construct
SEQUENCE: 21
atgctgcccg gtttggcact gctcctgctg gccgcctgga cggctcgggc gctggaggta   60
cccactgatg gtaatgctgg cctgctggct gaacccagat tgccatgtt ctgtggcaga   120
ctgaacatgc acatgaatgt ccagaatggg aagtgggatt cagatccatc agggaccaaa   180
acctgcattg ataccaagga aggcatcctg cagtattgcc aagaagtcta ccctgaactg   240
cagatcacca atgtggtaga agccaaccaa ccagtgacca tccagaactg gtgcaagcgg   300
ggccgcaagc agtgcaagac ccatccccac tttgtgattc cctaccgctg cttagttggt   360
gagtttgtaa gtgatgccct tctcgttcct gacaagtgca aattcttaca ccaggagagg   420
atggatgttt gcgaaactca tcttcactgg cacaccgtag ccaaagagac atgcagtgag   480
aagagtacca acttgcatga ctacggcatg ttgctgccct gcggaattga caagttccga   540
ggggtagagt ttgtgtgttg cccactggct gaagaaagtg acaatgtgga ttctgctgat   600
gcggaggagg atgactcgga tgtctggtgg ggcggagcag acacagacta tgcagatggg   660
agtgaagaca aagtagtaga agtagcagag gaggaagaag tggctgaggt ggaagaagaa   720
gaagccgatg atgacgagga cgatgaggat ggtgatgagg tagaggaaga ggctgaggaa   780
ccctacgaag aagccacaga gagaaccacc agcattgcca ccaccaccac caccaccaca   840
gagtctgtgg aagaggtggt tcgagtgtcc caaagtttac tcaagactac ccaggaacct   900
cttgcccgag atcctgttaa acttcctaca acagcagcca gtaccccctga tgccgttgac   960
aagtatctcg agacacctgg ggatgagaat gaacatgccc atttccagaa agccaaagag   1020
aggcttgagg ccaagcaccg agagagaatg tcccaggtca tgagagaatg ggaagaggca   1080
gaacgtcaag caaagaactt gcctaaagct gataagaagg cagttatcca gcatttccag   1140
gagaaagtgg aatctttgga acaggaagca gccaacgaga gacagcagct ggtggagca   1200
cacatggcca gagtggaagc catgctcaat gaccgccgcc gcctggccct ggagaactac   1260
atcaccgctc tgcaggctgt tcctcctcgg cctcgtcacg tgttcaatat gctaaagaag   1320
tatgtccgcg cagaacagaa ggacagacag cacaccctaa agcatttcga gcatgtgcgc   1380
atggtggatc ccaagaaagc cgctcagatc cggtcccagg ttatgacaca cctccgtgtg   1440
atttatgagc gcatgaatca gtctctctcc ctgctctaca cgtgcctgc agtggccgag   1500
gagattcagg atgaagttga tgagctgctt cagaaagagc aaaactattc agatgacgtc   1560
ttggccaaca tgattagtga accaaggatc agttacggaa acgatgctct catgccatct   1620
ttgaccgaaa cgaaaaccac cgtggagctc cttcccgtga tggagagtt cagcctggac   1680
gatctccagc cgtggcattc ttttggggct gactctgtac cagccaacac agaaaacgaa   1740
gttgagcctg ttgatgcccg ccctgctgcc gaccgaggac tgaccactcg accaggttct   1800
gggttgacaa atatcaagac ggaggagatc tctgaagtga agatggatgc agaattccga   1860
catgactcag gatatgaagt tcatcatcaa aaattggtgt tctttgcaga agatgtgggt   1920
tcaaacaaag gtgcaatcat tggactcatg gtgggcggtg ttgtcatagc cagtagtgatc   1980
gtcatcacct tggtgatgct gaagaagaaa cagtacacat ccattcatca tggtgtggtg   2040
gaggttgacg ccgctgtcac cccagaggag cgccacctgt ccaagatgca gcagaacggc   2100
tacgaaaatc caacctacaa gttctttgag cagatgcaga actag             2145

SEQ ID NO: 22         moltype = AA  length = 714
FEATURE               Location/Qualifiers
REGION                1..714
                      note = Protein encoded by novel APP mRNA
source                1..714
                      mol_type = protein
                      organism = synthetic construct
SEQUENCE: 22
MLPGLALLLL AAWTARALEV PTDGNAGLLA EPQIAMFCGR LNMHMNVQNG KWDSDPSGTK   60
TCIDTKEGIL QYCQEVYPEL QITNVVEANQ PVTIQNWCKR GRKQCKTHPH FVIPYRCLVG   120
EFVSDALLVP DKCKFLHQER MDVCETHLHW HTVAKETCSE KSTNLHDYGM LLPCGIDKFR   180
GVEFVCCPLA EESDNVDSAD AEEDDSDVWW GGADTDYADG SEDKVVEVAE EEEVAEVEEE   240
EADDDEDDED GDEVEEEAEE PYEEATERTT SIATTTTTTT ESVEEVVRVS QSLLKTTQEP   300
LARDPVKLPT TAASTPDAVD KYLETPGDEN EHAHFQKAKE RLEAKHRERM SQVMREWEEA   360
ERQAKNLPKA DKKAVIQHFQ EKVESLEQEA ANERQQLVET HMARVEAMLN DRRRLALENY   420
ITALQAVPPR PRHVFNMLKK YVRAEQKDRQ HTLKHFEHVR MVDPKKAAQI RSQVMTHLRV   480
IYERMNQSLS LLYNVPAVAE EIQDEVDELL QKEQNYSDDV LANMISEPRI SYGNDALMPS   540
LTETKTTVEL LPVNGEFSLD DLQPWHSFGA DSVPANTENE VEPVDARPAA DRGLTTRPGS   600
GLTNIKTEEI SEVKMDAEFR HDSGYEVHHQ KLVFFAEDVG SNKGAIIGLM VGGVVIATVI   660
VITLVMLKKK QYTSIHHGVV EVDAAVTPEE RHLSKMQQNG YENPTYKFFE QMQN          714

SEQ ID NO: 23         moltype = DNA  length = 25
FEATURE               Location/Qualifiers
misc_feature          1..25
                      note = NEP f primer
source                1..25
                      mol_type = other DNA
                      organism = synthetic construct
```

-continued

```
SEQUENCE: 23
cctggagatt cataatggat cttgt                                              25

SEQ ID NO: 24             moltype = DNA   length = 18
FEATURE                   Location/Qualifiers
misc_feature              1..18
                          note = NEP R primer
source                    1..18
                          mol_type = other DNA
                          organism = synthetic construct
SEQUENCE: 24
aaagggcctt gcggaaag                                                      18

SEQ ID NO: 25             moltype = DNA   length = 20
FEATURE                   Location/Qualifiers
misc_feature              1..20
                          note = APP F primer
source                    1..20
                          mol_type = other DNA
                          organism = synthetic construct
SEQUENCE: 25
gatccatcag ggaccaaaac                                                    20

SEQ ID NO: 26             moltype = DNA   length = 20
FEATURE                   Location/Qualifiers
misc_feature              1..20
                          note = APP R primer
source                    1..20
                          mol_type = other DNA
                          organism = synthetic construct
SEQUENCE: 26
agcggtaggg aatcacaaag                                                    20

SEQ ID NO: 27             moltype = DNA   length = 468
FEATURE                   Location/Qualifiers
misc_feature              1..468
                          note = target region of AON
source                    1..468
                          mol_type = other DNA
                          organism = synthetic construct
SEQUENCE: 27
taaattcctc agtaaatgtt tggtagatgc tgcctaataa accagtccag gttgccactg   60
ggaggattaa aagaagtaaa cgtgtataca tgaacagaga gacagtgcct tttcatgcta   120
aatgtggttc cccacatctc ctctgattag aggtgtgctc tgaacaagcc gagacggggc   180
cgtgccgagc aatgatctcc cgctggtact ttgatgtgac tgaagggaag tgtgccccat   240
tcttttacgg cggatgtggc ggcaaccgga acaactttga cacagaagag tactgcatgg   300
ccgtgtgtgg cagcgccagt aagtggaccc ttcttcgagc ctggccacct ttcgtctctc   360
tcgccactga ctctgctttt tgtaacagat tgattttcct ggttcttggg aatgggcctg   420
ttgctaccac taaccacatt tctgtccact tctctaattg ctcagagt              468

SEQ ID NO: 28             moltype = DNA   length = 357
FEATURE                   Location/Qualifiers
misc_feature              1..357
                          note = Target region of AON
source                    1..357
                          mol_type = other DNA
                          organism = synthetic construct
SEQUENCE: 28
atgttcattt tggttttgtt ggagggacca aacctaagtg agtgattttg tttgttaggt   60
tgtttttttg tcagtggact cgtgcatttc agccatcatt cccatgtttc tcttttttgtt  120
tttagttatg ttctcttatt ttttccatag tgtcccaaag tttactcaag actacccagg   180
aacctcttgc ccgagatcct gttaaacgta cgttgtcatt cacctgaggg aagggaagag   240
gggaggagga tgctgcttgg ttcacataac tccagcatca tcaccttctt tgcatggttt   300
tgtgtttctt gaacacctgt cttagtaaaa tgtttcttcc cattaccttg cttgtaa      357
```